(12) United States Patent
Park et al.

(10) Patent No.: US 12,405,242 B2
(45) Date of Patent: Sep. 2, 2025

(54) SYSTEMS AND METHODS FOR PATTERNING AND SPATIAL ELECTROCHEMICAL MAPPING OF CELLS

(71) Applicant: President and Fellows of Harvard College, Cambridge, MA (US)

(72) Inventors: Hongkun Park, Cambridge, MA (US); Jeffrey T. Abbott, Cambridge, MA (US); Wenxuan Wu, Cambridge, MA (US); Tianyang Ye, Cambridge, MA (US); Han Sae Jung, Cambridge, MA (US); Donhee Ham, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 18/240,894

(22) Filed: Aug. 31, 2023

(65) Prior Publication Data
US 2024/0255461 A1   Aug. 1, 2024

Related U.S. Application Data

(63) Continuation of application No. 17/940,174, filed on Sep. 8, 2022, now Pat. No. 11,774,396, which is a
(Continued)

(51) Int. Cl.
*G01N 27/327* (2006.01)
*B01J 19/08* (2006.01)
(Continued)

(52) U.S. Cl.
CPC ........ *G01N 27/3277* (2013.01); *B01J 19/087* (2013.01); *C12Q 1/02* (2013.01); *G01N 33/4836* (2013.01)

(58) Field of Classification Search
None
See application file for complete search history.

(56) References Cited

U.S. PATENT DOCUMENTS

| | | |
|---|---|---|
| 5,072,194 A | 12/1991 | Chevallier |
| 5,187,096 A | 2/1993 | Giaever et al. |

(Continued)

FOREIGN PATENT DOCUMENTS

| | | |
|---|---|---|
| CN | 1476536 A | 2/2004 |
| CN | 111220670 A | 6/2020 |

(Continued)

OTHER PUBLICATIONS

Invitation to Pay Additional Fees for Application No. PCT/US2016/012685 mailed Feb. 24, 2016.
(Continued)

*Primary Examiner* — J. Christopher Ball
(74) *Attorney, Agent, or Firm* — Wolf, Greenfield & Sacks, P.C.

(57) ABSTRACT

Disclosed herein are an apparatus for electrically assessing and/or manipulating cells. One aspect is directed to electrically mapping cells on the surface of the semiconductor substrate via cross-electrode impedance measurements. Further according to some aspects, the electrode array allows for spatially addressable electrical stimulation and/or recording of electrical signals in real-time using the CMOS circuitry. Some of these aspects are directed to using an electrode array to perform cell patterning through electrochemical gas generation, and extracellular electrochemical mapping.

20 Claims, 29 Drawing Sheets

Related U.S. Application Data continuation of application No. PCT/US2021/037630, filed on Jun. 16, 2021.

(60) Provisional application No. 63/040,439, filed on Jun. 17, 2020.

(51) Int. Cl.
*C12Q 1/02* (2006.01)
*G01N 33/483* (2006.01)

(56) References Cited

U.S. PATENT DOCUMENTS

| | | |
|---|---|---|
| 5,233,985 A | 8/1993 | Hudrlik |
| 5,605,612 A | 2/1997 | Park et al. |
| 6,032,062 A | 2/2000 | Nisch |
| 7,332,313 B2 | 2/2008 | Giaever et al. |
| 7,342,717 B1 | 3/2008 | Hausmann |
| 8,159,300 B2 | 4/2012 | Masuda et al. |
| 8,227,223 B2 | 7/2012 | Giaever et al. |
| 9,121,806 B1 | 9/2015 | Bhansali et al. |
| 9,360,469 B1 | 6/2016 | Clements et al. |
| 9,700,221 B2 | 7/2017 | Rajaraman et al. |
| 9,983,198 B2 | 5/2018 | Chvatal et al. |
| 11,167,131 B2 | 11/2021 | Isaacs et al. |
| 11,747,321 B2 | 9/2023 | Ham et al. |
| 11,768,196 B2 | 9/2023 | Ham et al. |
| 11,774,396 B2 | 10/2023 | Ham et al. |
| 11,833,346 B2 | 12/2023 | Park et al. |
| 12,174,140 B2 | 12/2024 | Ham et al. |
| 12,265,076 B2 | 4/2025 | Ham et al. |
| 2002/0010415 A1 | 1/2002 | Simon et al. |
| 2002/0045318 A1 | 4/2002 | Chen et al. |
| 2002/0182591 A1 | 12/2002 | Giaever et al. |
| 2002/0190732 A1 | 12/2002 | Cheng et al. |
| 2003/0100189 A1 | 5/2003 | Lee et al. |
| 2004/0100290 A1 | 5/2004 | Pope et al. |
| 2005/0173249 A1 | 8/2005 | Barlow et al. |
| 2005/0253137 A1 | 11/2005 | Whang et al. |
| 2005/0282284 A1 | 12/2005 | Rubinsky et al. |
| 2006/0121446 A1 | 6/2006 | Abassi et al. |
| 2007/0043301 A1 | 2/2007 | Martinsen et al. |
| 2007/0072257 A1 | 3/2007 | Negulescu et al. |
| 2007/0087401 A1 | 4/2007 | Neilson et al. |
| 2007/0187840 A1 | 8/2007 | Dell'Acqua-Bellavitis et al. |
| 2007/0264634 A1 | 11/2007 | Bock et al. |
| 2008/0009434 A1 | 1/2008 | Reches et al. |
| 2008/0218939 A1 | 9/2008 | Marcus et al. |
| 2009/0146735 A1 | 6/2009 | Jeong |
| 2009/0205201 A1 | 8/2009 | Xu et al. |
| 2009/0227066 A1 | 9/2009 | Joseph et al. |
| 2009/0255801 A1 | 10/2009 | Hass |
| 2010/0164110 A1 | 7/2010 | Jin et al. |
| 2010/0304425 A1 | 12/2010 | Speller |
| 2011/0210718 A1 | 9/2011 | Vana et al. |
| 2011/0233512 A1 | 9/2011 | Yang et al. |
| 2011/0253982 A1 | 10/2011 | Wang et al. |
| 2012/0094328 A1 | 4/2012 | Park et al. |
| 2012/0157804 A1 | 6/2012 | Rogers et al. |
| 2012/0182168 A1 | 7/2012 | Shibata et al. |
| 2013/0041235 A1 | 2/2013 | Rogers et al. |
| 2013/0041282 A1 | 2/2013 | Park et al. |
| 2013/0072775 A1 | 3/2013 | Rogers et al. |
| 2013/0115705 A1 | 5/2013 | Patolsky et al. |
| 2013/0123136 A1 | 5/2013 | Abassi et al. |
| 2013/0260467 A1 | 10/2013 | Park et al. |
| 2013/0338746 A1 | 12/2013 | Guvanasen et al. |
| 2013/0341734 A1 | 12/2013 | Merz |
| 2014/0001041 A1 | 1/2014 | Rahman et al. |
| 2014/0057283 A1 | 2/2014 | Wang et al. |
| 2015/0005680 A1 | 1/2015 | Lipani |
| 2015/0027885 A1 | 1/2015 | Rajaraman et al. |
| 2015/0148863 A1 | 5/2015 | Yun et al. |
| 2015/0376811 A1 | 12/2015 | Joung et al. |
| 2015/0377856 A1 | 12/2015 | Dunbar et al. |
| 2016/0047770 A1 | 2/2016 | Tyler et al. |
| 2016/0096173 A1 | 4/2016 | Teich et al. |
| 2016/0245788 A1 | 8/2016 | Wang et al. |
| 2016/0245790 A1 | 8/2016 | Kawai et al. |
| 2016/0278713 A1 | 9/2016 | Shoaran et al. |
| 2017/0058246 A1 | 3/2017 | Grier, Jr. et al. |
| 2017/0176414 A1 | 6/2017 | Abdolahad et al. |
| 2017/0220733 A1 | 8/2017 | Zhuang et al. |
| 2017/0336384 A1 | 11/2017 | Ino et al. |
| 2018/0163165 A1 | 6/2018 | Grier, Jr. et al. |
| 2018/0169403 A1 | 6/2018 | Park et al. |
| 2018/0246079 A1 | 8/2018 | Wang et al. |
| 2018/0252677 A1 | 9/2018 | Abdolahad et al. |
| 2020/0064336 A1 | 2/2020 | Zafar et al. |
| 2020/0292482 A1 | 9/2020 | Ham et al. |
| 2021/0187280 A1 | 6/2021 | Park et al. |
| 2021/0236033 A1 | 8/2021 | Butera et al. |
| 2021/0371846 A1 | 12/2021 | Ham et al. |
| 2022/0397512 A1 | 12/2022 | Ham et al. |
| 2023/0014082 A1 | 1/2023 | Ham et al. |
| 2023/0184739 A1 | 6/2023 | Ham et al. |
| 2024/0210380 A1 | 6/2024 | Ham et al. |
| 2024/0219370 A1 | 7/2024 | Ham et al. |
| 2024/0255461 A1 | 8/2024 | Park et al. |
| 2024/0325731 A1 | 10/2024 | Park et al. |

FOREIGN PATENT DOCUMENTS

| | | |
|---|---|---|
| DE | 19529371 C2 | 1/1998 |
| EP | 271 144 A1 | 1/2003 |
| JP | 2008-269725 A | 11/2008 |
| JP | 2009-510446 A | 3/2009 |
| JP | 2010-518885 A | 6/2010 |
| JP | 2016-529889 A | 9/2016 |
| JP | 2017-207410 A | 11/2017 |
| JP | 2018-132448 A | 8/2018 |
| WO | WO 2009/137440 A1 | 11/2009 |
| WO | WO 2012/050876 A2 | 4/2012 |
| WO | WO 2012/050881 A2 | 4/2012 |
| WO | WO 2016/112315 A2 | 7/2016 |
| WO | WO 2019/010343 A1 | 1/2019 |
| WO | WO 2019/089495 A1 | 5/2019 |
| WO | WO 2021/257686 A1 | 12/2021 |
| WO | WO 2021/257701 A1 | 12/2021 |
| WO | WO 2021/257705 A1 | 12/2021 |

OTHER PUBLICATIONS

International Search Report and Written Opinion for Application No. PCT/US2016/012685 mailed May 3, 2016.
International Preliminary Report on Patentability for PCT/US2016/012685 mailed Jul. 20, 2017.
Invitation to Pay Additional Fees for Application No. PCT/US18/58081 mailed Jan. 15, 2019.
International Search Report and Written Opinion for Application No. PCT/US18/58081 mailed Mar. 22, 2019.
International Preliminary Report on Patentability for Application No. PCT/US18/58081 mailed May 14, 2020.
International Search Report and Written Opinion for Application No. PCT/US2021/037604 mailed Sep. 29, 2021.
International Preliminary Report on Patentability for Application No. PCT/US2021/037604 mailed Dec. 29, 2022.
International Search Report and Written Opinion for Application No. PCT/US2021/37626 mailed Sep. 22, 2021.
International Preliminary Report on Patentability for Application No. PCT/US2021/37626 mailed Dec. 29, 2022.
International Search Report and Written Opinion for Application No. PCT/US2021/037630 mailed Sep. 28, 2021.
International Preliminary Report on Patentability No. PCT/US2021/037630 mailed Dec. 29, 2022.
Invitation to Pay Additional Fees for Application No. PCT/US18/40969 mailed Aug. 31, 2018.
International Search Report and Written Opinion for Application No. PCT/US18/40969 mailed Nov. 2, 2018.
International Preliminary Report on Patentability for Application No. PCT/US18/40969 mailed Jan. 16, 2020.

(56) References Cited

OTHER PUBLICATIONS

Abbott et al., CMOS nanoelectrode array for all-electrical intracellular electrophysiological imaging. Nat Nanotechnol. May 2017;12(5):460-466 and supplemental information. doi: 10.1038/nnano.2017.3. Epub Feb. 13, 2017. 37 pages.
Abbott et al., Multi-parametric functional imaging of cell cultures and tissues with a CMOS microelectrode array. Lab Chip. Mar. 29, 2022;22(7):1286-1296. doi: 10.1039/d1lc00878a.
Crescentini et al., Noise limits of CMOS current interfaces for biosensors: a review. IEEE Trans Biomed Circuits Syst. 2014;8(2):278-292.
Giovangrandi et al., Low-cost microelectrode array with integrated heater for extracellular recording of cardiomyocyte cultures using commercial flexible printed circuit technology. Sensors and Actuators B 113. Jan. 17, 2006;113:545-554. Epub Apr. 22, 2005.
Jorgolli, Integrated Nanoscale Tools for Interrogating Living Cells. May 2015. Doctoral dissertation, Harvard University, Graduate School of Arts & Sciences.
Kim et al., An area-efficient low-noise CMOS DNA detection sensor for multichannel nanopore applications. Sensors and Actuators B: Chemical. Jan. 2013;176:1051-1055.
Laborde et al., Real-time imaging of microparticles and living cells with CMOS nanocapacitor arrays. Nat Nanotechnol. Sep. 2015;10(9):791-5. doi: 10.1038/nnano.2015.163. Epub Aug. 3, 2015.
Park et al., 1024-Pixel CMOS Multimodality Joint Cellular Sensor/Stimulator Array for Real-Time Holistic Cellular Characterization and Cell-Based Drug Screening. IEEE Trans Biomed Circuits Syst. Feb. 2018; 12(1): 80-94. Author manuscript provided. 45 pages.
U.S. Appl. No. 18/501,690, filed Nov. 3, 2023, Park et al.
U.S. Appl. No. 16/760,723, filed Apr. 30, 2020, Ham et al.
U.S. Appl. No. 17/891,964, filed Aug. 19, 2022, Ham et al.
U.S. Appl. No. 18/365,045, filed Aug. 3, 2023, Ham et al.
U.S. Appl. No. 18/365,172, filed Aug. 3, 2023, Abbott et al.
PCT/US2016/012685, Feb. 24, 2016, Invitation to Pay Additional Fees.
PCT/US2016/012685, May 3, 2016, International Search Report and Written Opinion.
PCT/US2016/012685, Jul. 20, 2017, International Preliminary Report on Patentability.
PCT/US18/58081, Jan. 15, 2019, Invitation to Pay Additional Fees.
PCT/US18/58081, Mar. 22, 2019, International Search Report and Written Opinion.
PCT/US18/58081, May 14, 2020, International Preliminary Report on Patentability.
PCT/US2021/037604, Sep. 29, 2021, International Search Report and Written Opinion.
PCT/US2021/037604, Dec. 29, 2022, International Preliminary Report on Patentability.
PCT/US2021/37626, Sep. 22, 2021, International Search Report and Writtin Opinion.
PCT/US2021/37626, Dec. 29, 2022, International Preliminary Report on Patentability.
PCT/US2021/037630, Sep. 28, 2021, International Search Report and Written Opinion.
PCT/US2021/037630, Dec. 29, 2022, International Preliminary Report on Patentability.
PCT/US18/40969, Aug. 31, 2018, Invitation to Pay Additional Fees.
PCT/US18/40969, Nov. 2, 2018, International Search Report and Written Opinion.
PCT/US18/40969, Jan. 16, 2020, International Preliminary Report on Patentability.
Guo et al., Controllable in-situ cell electroporation with cell positioning and impedance monitoring using micro electrode array. Sci Rep. Aug. 10, 2016;6:31392(1-8). doi: 10.1038/srep31392.
Park et al., A microsystem for sensing and patterning oxidative microgradients during cell culture. Lab Chip. May 2006;6(5):611-22. doi: 10.1039/b516483d. Epub Mar. 16, 2006.
Rahman et al., CellMap: An automated multielectrode array cell culture analysis system based on electrochemical impedance spectroscopy. <https://digitalcommons.usf.edu/etd/586> Retrieved on May 30, 2024. USF Tampa Graduate Theses and Dissertations. Jun. 28, 2007;1-153.
Extended European Search Report mailed Jun. 7, 2024 for Application No. EP 21825487.8.
Japanese Office Action mailed Dec. 10, 2024 for Application No. JP 2022-577744.
Extended European Search Report mailed May 31, 2024 for Application No. EP 21825407.6.
Japanese Office Action mailed Mar. 5, 2025 for Application No. JP 2022-577391.
Partial Supplementary European Search Report mailed Jun. 12, 2024 for Application No. EP 21825109.8.
Extended European Search Report mailed Sep. 2, 2024 for Application No. EP 21825109.8.
Singapore Search Report and Written Opinion dated Jul. 3, 2024 for Application No. SG 11202261181P.
Abbott et al., A nanoelectrode array for obtaining intracellular recordings from thousands of connected neurons. Nat Biomed Eng. Feb. 2020;4(2):232-241. doi: 10.1038/s41551-019-0455-7. Epub Sep. 23, 2019.
Abbott et al., Optimizing nanoelectrode arrays for scalable intracellular electrophysiology. Accounts of Chem Res. Feb. 13, 2018;51(3):600-608.
Lopez et al., A multimodal CMOS MEA for high-throughput intracellular action potential measurements and impedance spectroscopy in drug-screening applications. IEEE Journal of Solid-State Circuits. Nov. 2, 2018;53(11):3076-86.
Chinese Office action mailed Mar. 17, 2025 for Application No. CN 202180058242.4.

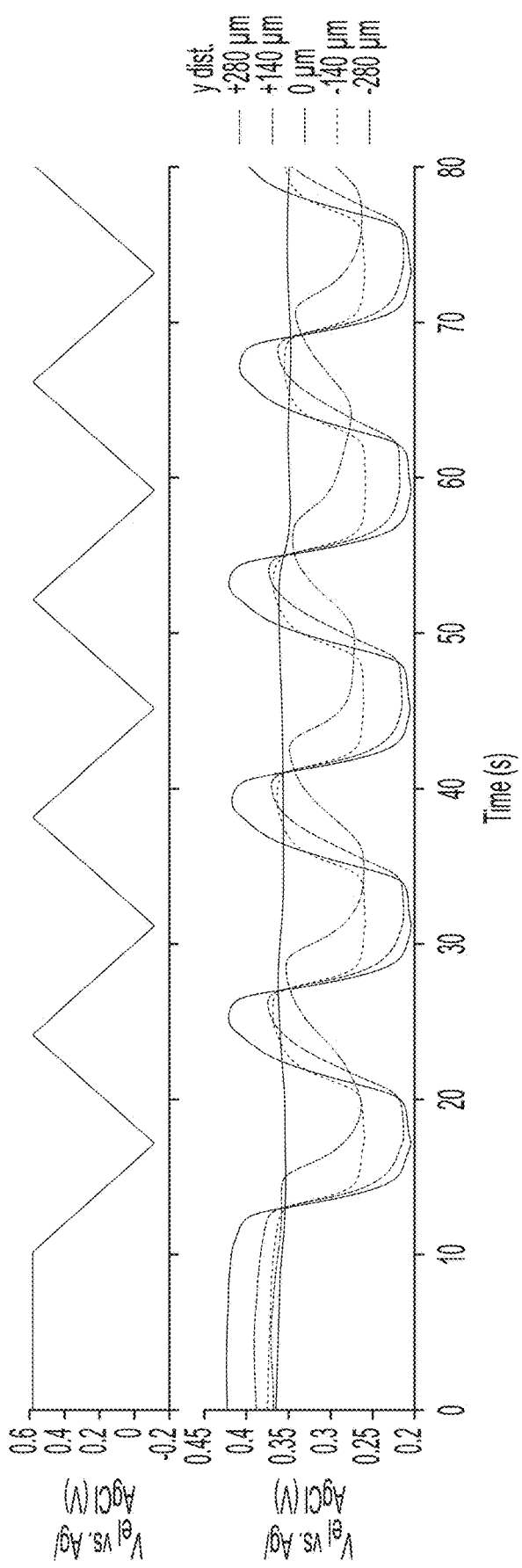
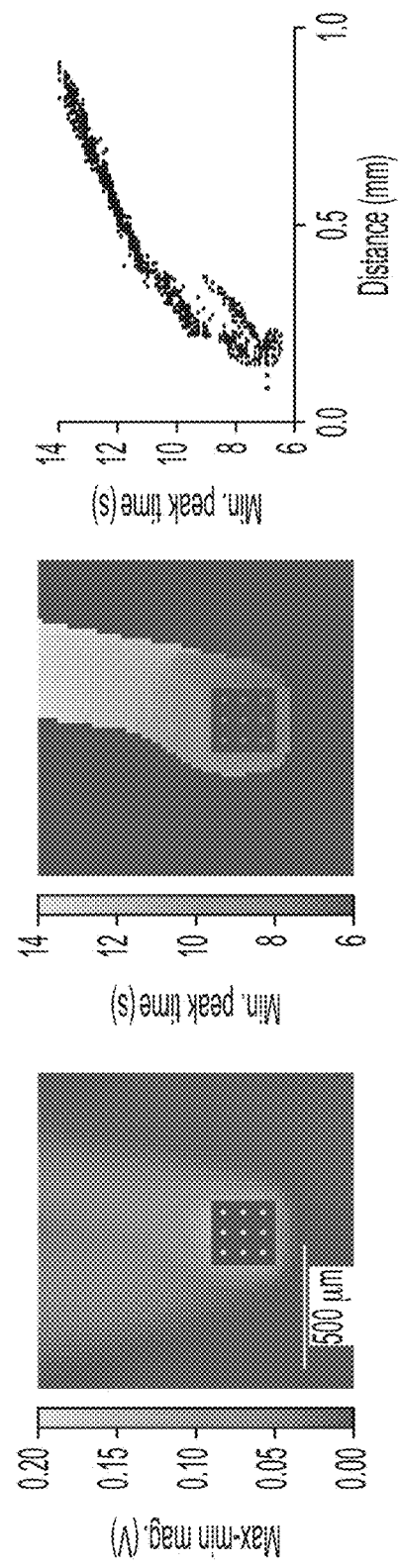
FIG. 21a
FIG. 21b
FIG. 21c

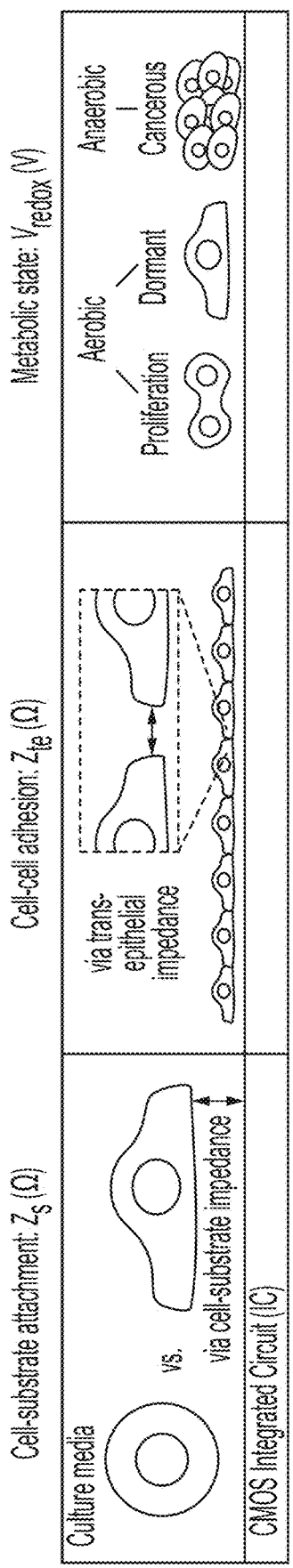
FIG. 23a
FIG. 23b
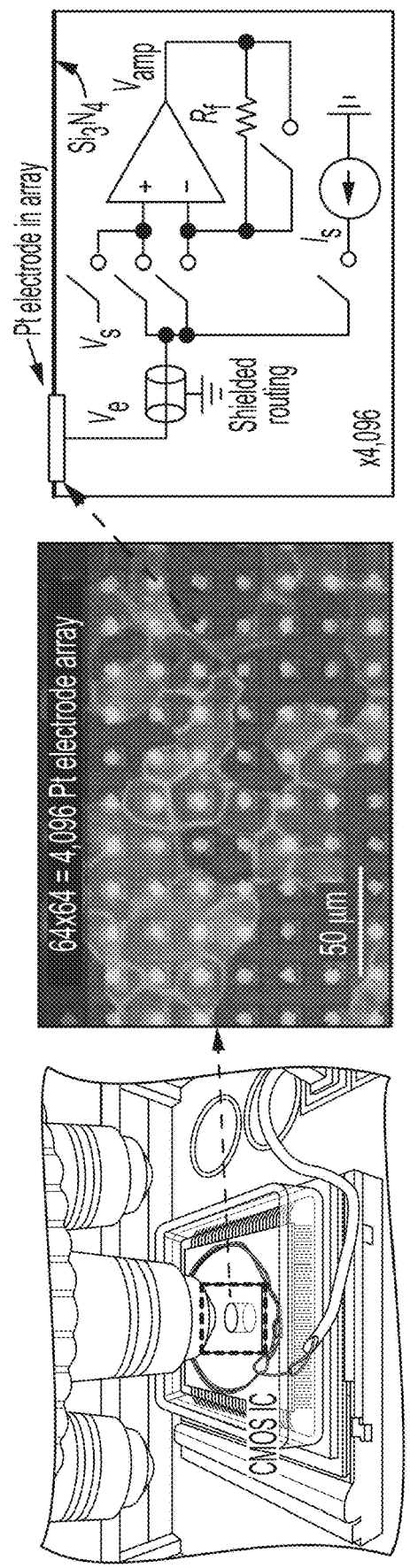
FIG. 23c
FIG. 23d

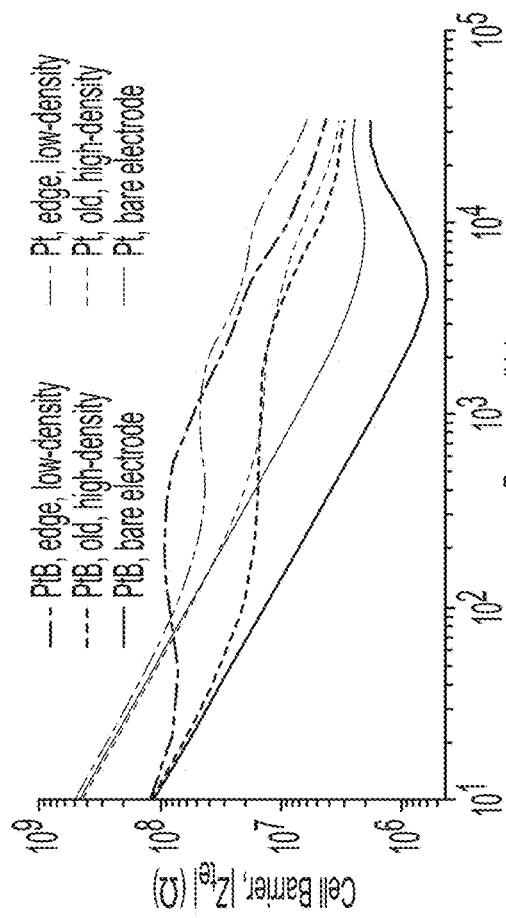
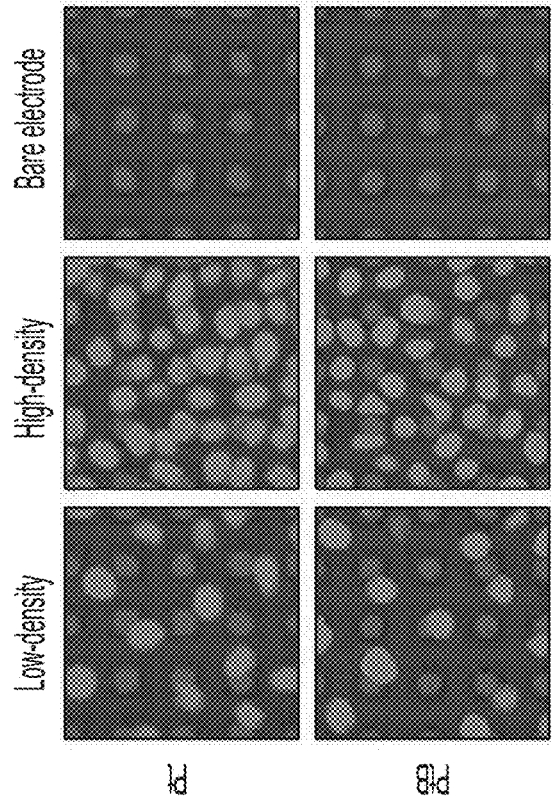
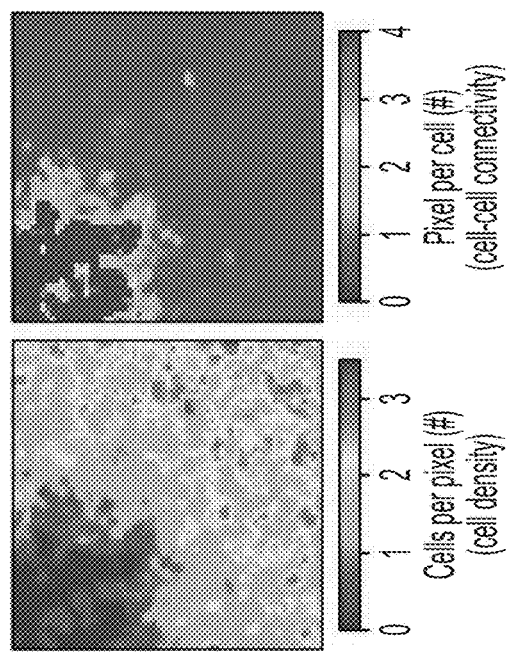
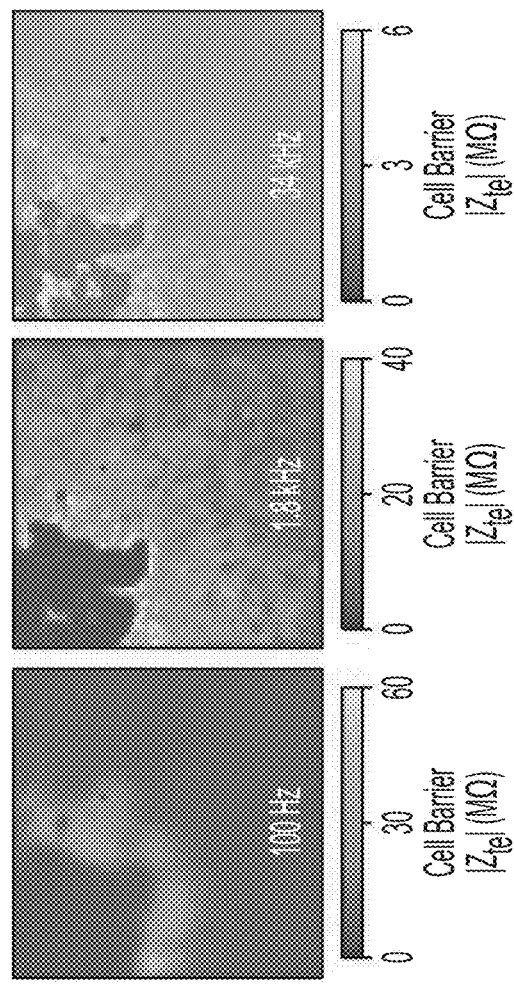
FIG. 26a
FIG. 26b
FIG. 26c
FIG. 26d

[1]

SYSTEMS AND METHODS FOR PATTERNING AND SPATIAL ELECTROCHEMICAL MAPPING OF CELLS

CROSS-REFERENCE TO RELATED APPLICATIONS

This application is a continuation of U.S. patent application Ser. No. 17/940,174, filed Sep. 8, 2022, which is a continuation of International Application No.: PCT/US2021/037630, filed Jun. 16, 2021, entitled "Systems and Methods for Patterning and Spatial Electrochemical Mapping of Cells," by Park, et al., which claims the benefit of U.S. Provisional Patent Application Ser. No. 63/040,439, filed Jun. 17, 2020, entitled "Systems and Methods for Patterning and Spatial Electrochemical Mapping of Cells," by Park, et al. each of which is incorporated herein by reference in its entirety.

BACKGROUND

The present disclosure relates to a semiconductor device for electrically assessing cells or other biological specimens.

SUMMARY OF THE DISCLOSURE

Disclosed herein are various apparatuses for electrically assessing and/or manipulating cells. One aspect is directed to electrically mapping cells on the surface of the semiconductor substrate via cross-electrode impedance measurements. Further according to some aspects, the electrode array allows for spatially addressable electrical stimulation and/or recording of electrical signals in real-time using the CMOS circuitry. Some of these aspects are directed to using an electrode array to perform cell patterning through electrochemical gas generation, and extracellular electrochemical mapping.

Some embodiments relate to an apparatus for mapping one or more cells. The apparatus comprises a semiconductor substrate. The semiconductor substrate comprises a plurality of electrodes exposed at a surface of the semiconductor substrate; active circuitry coupled to the plurality of electrodes and configured to measure a first set of cross-electrode currents between a first electrode of the plurality of electrodes and some or all of the remaining electrodes; measure a second set of cross-electrode currents between a second electrode of the plurality of electrodes and some or all of the remaining electrodes. The apparatus further comprises one or more processors configured to receive the measured cross-electrode currents from the active circuitry and to generate a map of the one or more cells based on the first set and second set of cross-electrode currents.

In some embodiments, the active circuitry is further configured to apply a stimulus signal at the first electrode of the plurality of electrodes, and to apply a reference voltage at the remaining electrodes where the cross-electrode currents are being measured from. The stimulus signal may have a frequency of less than 10 KHz and preferably between 0.1 and 5 kHz. The plurality of electrodes may be arranged in an array having a pitch of less than 30 µm and preferably less than 5 µm. The semiconductor substrate may comprise silicon. The semiconductor substrate may comprise a silicon substrate, and the active circuitry may comprise complimentary metal-oxide semiconductor (CMOS) components in the silicon substrate. The plurality of electrodes may comprise a plurality of pads disposed on an insulative surface of the semiconductor substrate. The active circuitry may comprise a plurality of recording circuits, each recording circuit configured to measure a current at an electrode of the plurality of electrodes. The plurality of recording circuits may comprise at least 8 recording circuits, at least 10 recording circuits, and preferably at least 4000 recording circuits. Each recording circuit may comprise a transimpedance amplifier (TIA). The TIA may comprise an impedance component having a resistance of at least 10 MΩ, at least 100 MΩ, or between 10 MΩ and 1 GΩ, wherein an output voltage of the TIA is proportional to a voltage across the impedance component. The impedance component may comprise a switching capacitor. The one or more cells may be disposed in a first well of a multi-well plate, and the plurality of electrodes may be a first electrode array exposed to the first well, and the apparatus further may comprise a second electrode arrays exposed on the surface of the semiconductor substrate, and exposed to a second well of the multi-well plate. The multi-well plate may comprise at least 24, at least 96, or at least 384 wells. The plurality of electrodes may be sized such that more than one electrode are configured to be in contact with one cell of the one or more cells. The plurality of pads may comprise Au. The plurality of pads may comprise Pt.

Some embodiments relate to a method for mapping one or more cells in contact with an electrode array disposed on a surface area of a semiconductor substrate. Each electrode in the electrode array has an electrode location on the surface area. The method comprises for each electrode of at least one electrode of the electrode array, applying a stimulus signal at the electrode; measuring a set of cross-electrode currents between the electrode and some or all of the remaining electrodes in the electrode array; generating a representative value associated with the electrode location of the electrode based on the set of cross-electrode currents; and generating a map of representative values on the surface area based on the generated representative values and respective associated electrode locations of the at least one electrode.

In some embodiments, generating the representative value comprises selecting a maximum current value of the set of cross-electrode current as the representative value. Generating the representative value may comprise selecting a maximum current value of the set of cross-electrode current as the representative value. The at least one electrode may include all electrodes in the electrode array. The map may have a spatial resolution of 20 µm or less and preferably 5 µm or less.

In some embodiments, the generated map is a first map generated at a first time and comprises a plurality of pixels, and the method further comprises: generating a second map of representative values on the surface area at a second time subsequent to the first time, wherein the second map comprises a plurality of pixels; determining a first count of pixels in the first map having a representative value within a predetermined range; determining a second count of pixels in the second map having a representative value within the predetermined range; and determining a cell adhesion characteristic based on a comparison of the first count with the second count. The map may comprise a plurality of pixels, each pixel associated with a representative value. The at least one electrode may comprise a first electrode having a first electrode location and a second electrode having a second electrode location, the first electrode and the second electrode adjacent each other on the surface area, and the map may comprise a first pixel and a second pixel corresponding to the first electrode location and the second electrode location, respectively. Generating the map may comprise determining an up-scaled representative value associated with a third pixel between the first and second pixels. Determining the up-scaled representative value may comprise calculating an up-scaled electrode current by dividing a cross-electrode current $I_{12}$ between the first and second electrode when a stimulus signal is applied at the second electrode with a product of a first current $I_1$ and a second current $I_2$, wherein $I_1$ is a sum of cross-electrode currents measured at all of the remaining electrodes when a stimulus signal is applied at the first electrode, and $I_2$ is a sum of cross-electrode currents measured at all of the remaining electrodes when a stimulus signal is applied at the second electrode. A number of pixels in the map may be more than a number of electrodes in the electrode array. Electrode locations in the electrode array may be arranged in a plurality of rows and a plurality of columns. The electrode array may have M rows and N columns, and the map may have at least 3M×3N pixels.

Some embodiments relate to a system for mapping one or more cells. The system comprises a plurality of electrodes exposed at a surface area of a semiconductor substrate; circuitry disposed in the semiconductor substrate that is controllable to apply a stimulus signal and/or measure a current at one or more electrodes of the plurality of electrodes; at least one non-transitory computer-readable medium having stored thereon executable instructions; and at least one processor programmed by the executable instructions to perform a method. The method comprises acts of: for each electrode in the plurality of electrodes, controlling the circuitry to apply a stimulus signal at the electrode; controlling the circuitry to measure a set of cross-electrode currents between the electrode and some or all of the remaining electrodes in the plurality of electrodes; generating a representative value associated with the electrode location of the electrode based on the set of cross-electrode currents; and generating a map of representative values on the surface area based on the generated representative values and respective associated electrode locations of the plurality of electrodes.

In some embodiments, generating the representative value comprises: selecting a maximum current value of the set of cross-electrode current as the representative value. Generating the representative value may comprise selecting a maximum current value of the set of cross-electrode current; and calculating an impedance based on the selected maximum current value as the representative value. The map may comprise a plurality of pixels, each pixel associated with a representative value. The plurality of electrodes may comprise a first electrode having a first electrode location and a second electrode having a second electrode location, the first electrode and the second electrode adjacent each other on the surface area. The map may comprise a first pixel and a second pixel corresponding to the first electrode location and the second electrode location, respectively, and generating the map may comprise determining an up-scaled representative value associated with a third pixel between the first and second pixels.

Some embodiments relate to a method for providing spatially positioned electrochemical reactions with an electrode array exposed on a surface of a semiconductor substrate. The method comprises selecting one or more electrodes in the electrode array; controlling circuitry in the semiconductor substrate to apply, at the one or more electrodes, one or more stimulus signals to initiate an electrochemical reaction at the one or more electrodes.

In some embodiments, the electrochemical reaction may be a half reaction that generates a gas in a solution, and the one or more stimulus signals may comprise potentials that are above a redox potential for generation of the gas. The solution may comprise a plurality of cells attached to the surface of the semiconductor substrate, and the method may further comprise: generating the gas at the selected one or more electrodes such that at least one cell of the plurality of cells that is disposed on the selected one or more electrodes is detached from the surface of the semiconductor substrate. The gas may comprise $H_2$, $Cl_2$, or $O_2$. The plurality of cells may be a plurality of cells of a first type, and the method may further comprise: plating one or more cells of a second type on the surface of the semiconductor substrate at locations where the at least one cell of the first type has detached from. In some embodiments, the method may further comprise: mapping a time sequence of regrowth of the plurality of cells on the surface at positions where the at least one cell has detached from; and based on the mapping, determining a growth rate of the plurality of cells. Controlling circuitry to apply one or more pre-determined potentials may comprise performing cyclic voltammetry at the selected one or more electrodes, and the method may further comprise: measuring, with the circuitry, a value of an electrical characteristic at each of some or all remaining electrodes in the electrode array that are outside the selected one or more electrodes; and generating a map of electrical characteristics based on the result of the measuring. The electrical characteristic may be a characteristic of an open-circuit potential. The electrical characteristic may be a current. The characteristic of the current may be a maximum extent of a range of a cyclic current.

In some embodiments, controlling circuitry to apply one or more pre-determined potentials may comprise applying a pulsed voltage signal at an electrode of the selected one or more electrodes. During a first portion within the pulsed voltage signal, the electrode is being oxidized, and during a second portion of the pulsed voltage signal, an oxide on the electrode is being reduced, and the method may further comprise: measuring, with the circuitry, a current signal at the electrode during the second portion of the pulsed voltage signal; based on a time rate of change of the current signal, determining an oxygen concentration at a position of the electrode; and generating a map of oxygen concentration based on the result of the determining. The one or more potentials may be relative to a potential of a reference electrode.

Some embodiments relate to a system. The system comprises a semiconductor substrate. The semiconductor substrate comprises an electrode array including a plurality of individually addressable electrodes disposed on a surface of the semiconductor substrate; and circuitry that is controllable by one or more processors to apply, at a group of electrodes in the electrode array, one or more potentials relative to a potential of an electrode in the electrode array or a potential of a reference electrode to initiate an electrochemical reaction at the group of electrodes.

In some embodiments, the electrode array may comprise a plurality of pads disposed on an insulative surface of the semiconductor substrate. The plurality of pads may comprise Au or Pt. The reference electrode may be a Ag/AgCl reference electrode. The electrode array may comprise at least 1000, at least 4000, or at least 1,000,000 electrodes, and the circuitry may comprise a plurality of recording circuits, each recording circuit configured to measure a current at an electrode of the electrode array. The plurality of recording circuits may comprise at least 10 recording circuits, or at least 4000 recording circuits. Each recording circuit may comprise a transimpedance amplifier (TIA). The TIA may comprise an impedance component having a resistance of at least 10 MΩ, wherein an output voltage of the TIA is proportional to a voltage across the impedance component. The impedance component may comprise a switching capacitor.

Some embodiments relate to a system for providing spatially positioned electrochemical reactions. The system comprises an electrode array exposed at a surface area of a semiconductor substrate; circuitry disposed in the semiconductor substrate and coupled to the electrode array; at least one non-transitory computer-readable medium having stored thereon executable instructions; and at least one processor programmed by the executable instructions to perform a method. The method comprises acts of: selecting a pattern of electrodes in the electrode array; and controlling circuitry to apply, at the pattern of electrodes, one or more pre-determined potentials relative to a potential of an electrode in the electrode array or a potential of a reference electrode, such that an electrochemical reaction is initiated at the pattern of electrodes.

BRIEF DESCRIPTION OF THE DRAWINGS

Various aspects and embodiments will be described with reference to the following figures. It should be appreciated that the figures are not necessarily drawn to scale. Items appearing in multiple figures are indicated by the same reference number in all the figures in which they appear. In the drawings:

FIG. 1b is a two-dimensional data plot of a simulated voltage distribution in the apparatus shown in FIG. 1a;

FIG. 2b is a schematic side view diagrams illustrating a scenario where a cell is disposed over some electrodes of the electrode array in FIG. 2a;

FIG. 21a illustrates data plots that show select electrode voltages plotted over time;

FIG. 21b-c is a heat map that illustrates for one cycle, the overall amplitude of the open circuit potential plotted across the array;

FIG. 23a shows a series of schematic diagrams illustrating electrical imaging of three parameters useful for live-cell assessment;

FIG. 23b is an image illustrating a fluidic well packaged on top of a chip mounted below a microscope for simultaneous optical and electrical measurements;

FIG. 23c is a colorized microscope image illustrating cells and an electrode array;

FIG. 23d is a schematic diagram illustrating an electrode connected to an exemplary pixel circuit;

FIG. 26a is a series of fluorescent images illustrating results of a comparison study of electrode impedance under three scenarios;

FIG. 26b is a data plot illustrating that PtB lowered the $Z_{te}$ measurement of bare electrodes;

FIG. 26c illustrates cell barrier maps versus a reference at different frequencies;

FIG. 26d shows cell density and connectivity maps extracted from the nuclei of the fluorescence images;

DETAILED DESCRIPTION

The present disclosure is directed to various apparatuses for electrically assessing and/or manipulating cells. In one embodiment, the apparatus includes a semiconductor substrate having complimentary metal-oxide semiconductor (CMOS) circuitry electrically interfaced with an electrode array that can also be fabricated using CMOS-compatible fabrication techniques on a surface of the semiconductor substrate and exposed to the cells. The inventors have recognized and appreciated that by using semiconductor processing techniques, an electrode array may be fabricated and integrated with active circuitry in an economical fashion. Furthermore, electrodes in an electrode array having a small electrode size and electrode-to-electrode pitch may allow for higher spatial-resolution assessment of multiple cells compared to using an electrode that is larger than a size of a cell. For example, individual cells may be distinguishable when mapped using a high density electrode array, compared to a large electrode covered by an ensemble of cells. Further according to some aspects, the electrode array allows for spatially addressable electrical stimulation and/or recording of electrical signals in real-time using the CMOS circuitry. Some of these aspects are directed to using an electrode array to perform cell patterning through electrochemical gas generation, and extracellular electrochemical mapping.

One aspect is directed to electrically mapping cells on the surface of the semiconductor substrate via cross-electrode impedance measurements. The inventors have recognized and appreciated that electrical impedance measured between two electrodes, or cross-electrode impedance, may be affected by impedance along a current path between the electrodes. As a result presence of one or more cells along the current path may affect the cross-electrode impedance, such that cells can be mapped using cross-electrode impedance measurements.

Figure 1B:
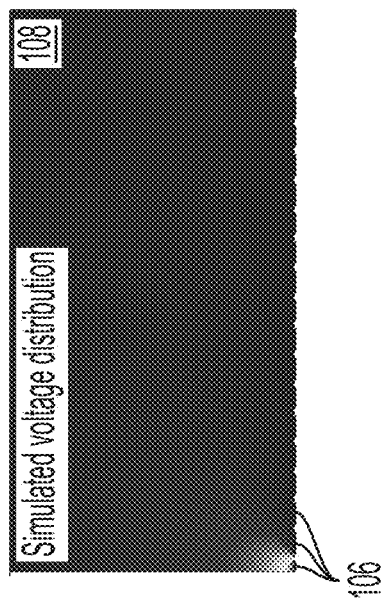
Figure 1C:
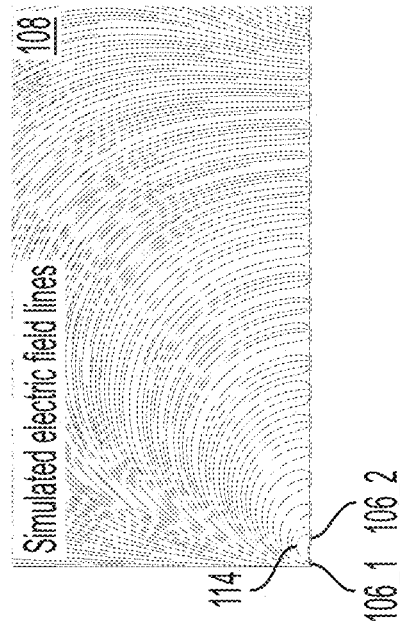
FIG. 1c is a data plot of simulated electric field lines corresponding to the example shown in FIG. 1b.
Figure 1A:
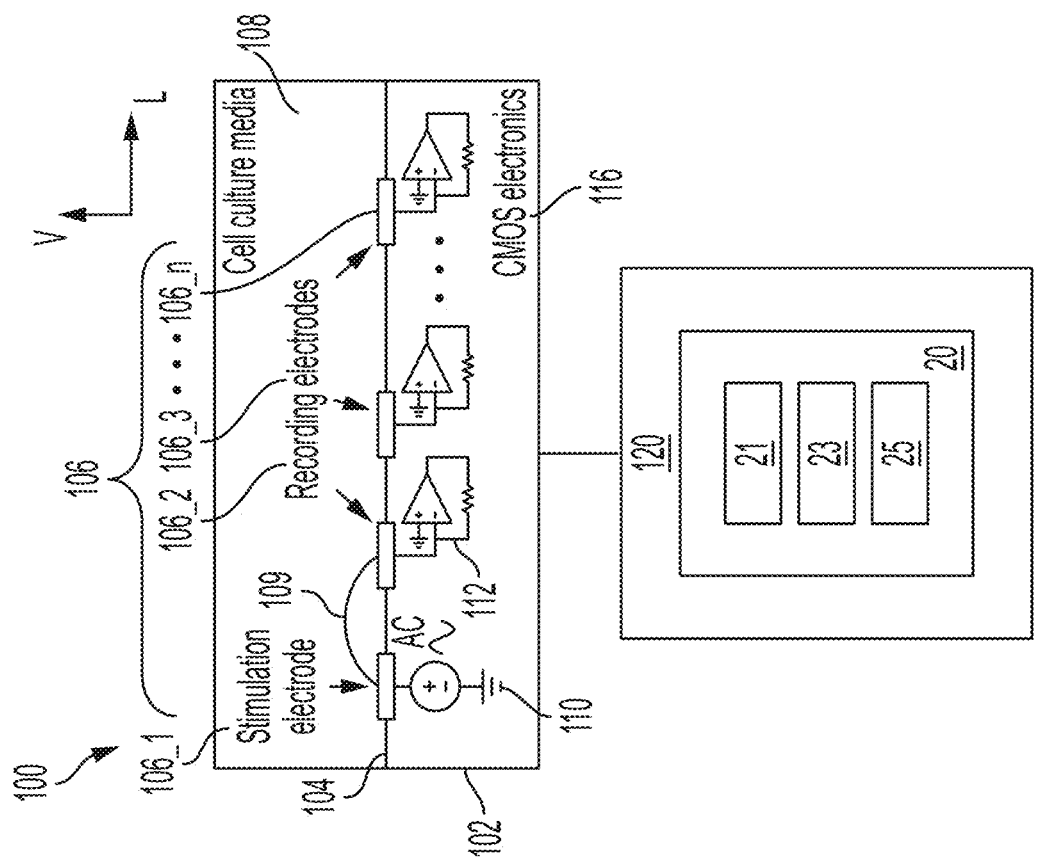
FIG. 1a is a schematic side view diagram of a semiconductor substrate, in accordance with some embodiments.

FIG. 1a is a schematic side view diagram of a semiconductor substrate, in accordance with some embodiments. FIG. 1a shows an apparatus 100 that has an electrode array 106 that includes a plurality of electrodes 106_1, 106_2, 106_3 . . . 106_n disposed on a surface 104 of a semiconductor substrate 102. FIG. 1a illustrates an example of cross-electrode impedance measurement by applying a voltage stimulus to a first electrode such as 106_1, and measuring a current at a second electrode such as 106_2. The measured current, also referred to as a cross-electrode current between electrodes 106_1 and 106_2 flows along one or more current paths 109 in a medium 108 that is in contact with the electrode array 106. Electrode 106_1 may be connected to a stimulus source circuit 110, and may be referred to as a stimulation electrode. Electrode 106_2 may be connected to a current measuring circuit 112, and may be referred to as a recording electrode.

Cross-electrode impedance between electrodes 106_1 and 106_2 may be obtained from the values of cross-electrode current and stimulus voltage between the pair of electrodes using any suitable method known in the art, for example by dividing the stimulus voltage amplitude with the cross-electrode current amplitude. A processing unit 120 may be provided that receives signals from active circuitry within the semiconductor substrate 102 and performs the determination of the cross-electrode impedance. It should be appreciated that there is no requirement to calculate the actual impedance values, and that any representative measurement that is indicative of impedance between two electrodes may be used. Alternatively or in addition to calculating the impedance value, the cross-electrode current may be used as an indicator for the cross-electrode impedance when measurements at different electrodes are compared, if the stimulus voltage amplitude is programmed to be a known constant.

FIG. 1b is a two-dimensional data plot of a simulated voltage distribution in the apparatus shown in FIG. 1a, and shows that when a voltage is applied to a stimulation electrode 106_1, the potential in the medium 108 falls off both along the vertical direction (V) and lateral direction (L) away from the stimulation electrode 106_1. FIG. 1c is a data plot of simulated electric field lines corresponding to the example shown in FIG. 1b. FIG. 1c shows that electric field lines 114 that emanate from stimulation electrode 106_1 flows along a line that is directed upward from electrode 106_1, curves laterally toward recording electrodes such as the recording electrode 106_2, before directed downward to terminate at the recording electrode 106_2.

Figure 2A:
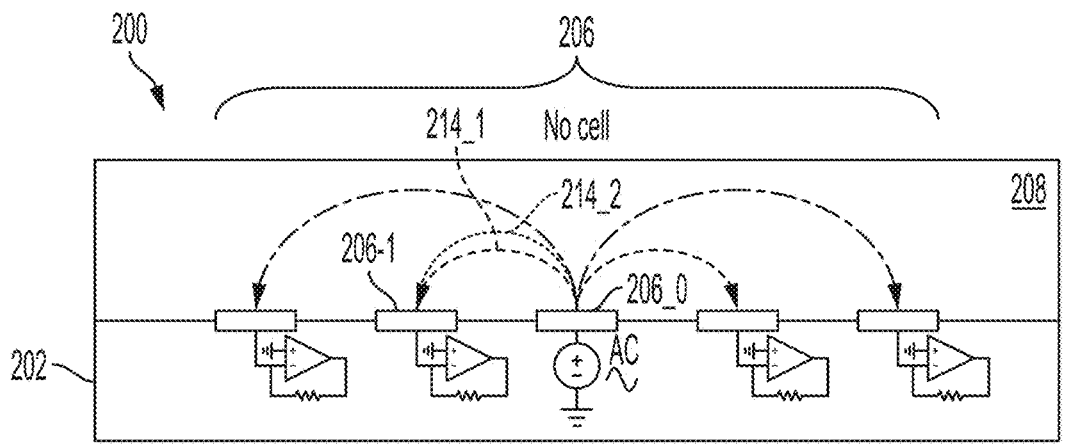
FIG. 2a is a schematic side view diagram of an apparatus with a semiconductor substrate without the presence of a cell, in accordance with some embodiments.
Figure 2B:
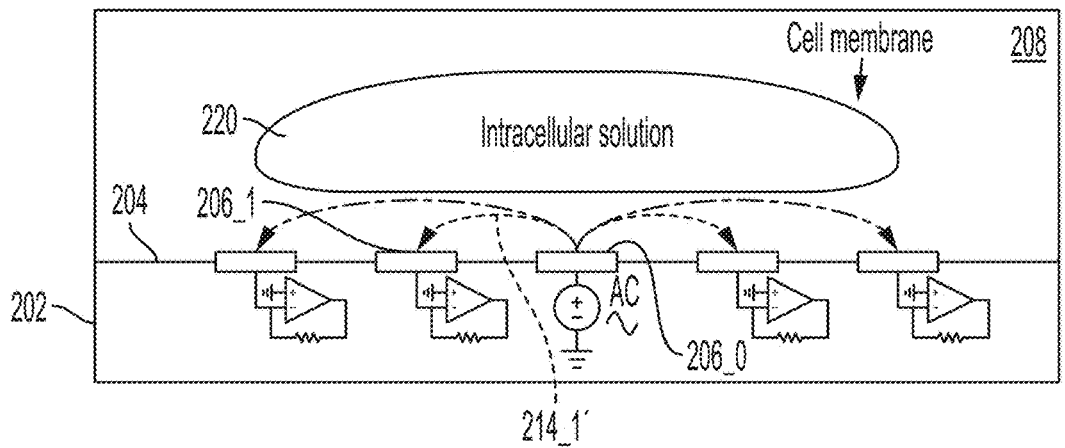
Figure 2C:
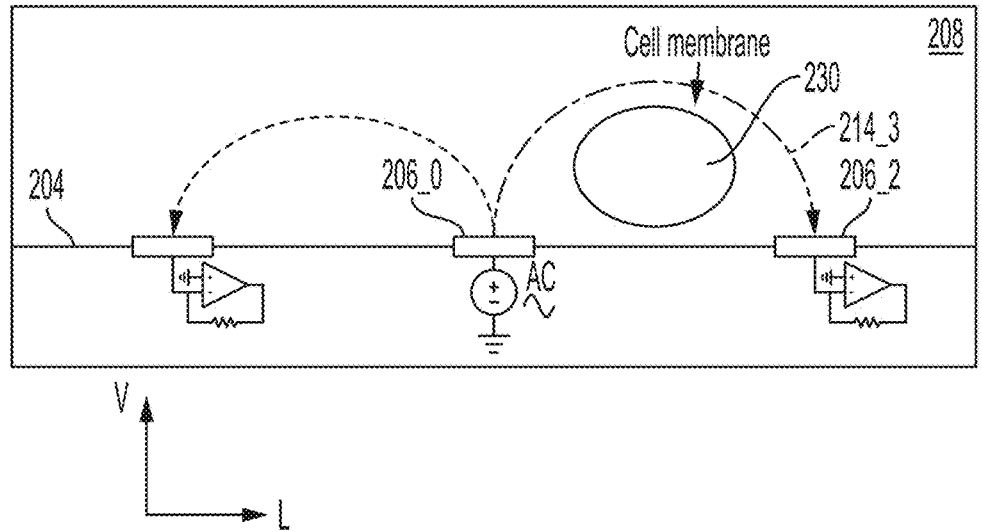
FIG. 2c is a schematic side view diagrams illustrating scenario where a cell is disposed outside the electrode array in FIG. 2a and in between some electrodes.

The presence of cells may alter the shape and distribution of electric field lines 114 between electrodes and in turn lead to a change in cross-electrode impedance, as discussed in detail below in relation to FIG. 2. FIG. 2a is a schematic side view diagram of an apparatus 200 with a semiconductor substrate 202 without the presence of a cell, in accordance with some embodiments. In FIG. 2a, electrode 206_0 of an electrode array 206 is configured to be a stimulus electrode, with electric fields lines 214_1 and 214_2 linking stimulus electrode 206_0 and recording electrode 206_1. FIG. 2b is a schematic side view diagrams illustrating a scenario where a cell 220 is disposed over some electrodes of the electrode array in FIG. 2a. FIG. 2c is a schematic side view diagrams illustrating scenario where a cell 230 is disposed outside the electrode array in FIG. 2a and in between some electrodes.

The inventors have recognized and appreciated that biological cells have a lipid bilayer that forms a continuous membrane barrier around the cell. Electrically, the membrane can behave as a capacitor in parallel with a high resistance, and can have a different electrical impedance compared to the surrounding medium such as a solution containing the cells. A cell with its high-impedance membrane on top of the electrode array will then affect the current distribution in the solution such as solution 208 in FIGS. 2a-2c. In FIG. 2c, a suspended cell blocks field lines in the solution and lowers the nearest neighbor coupling between electrodes. In contrast, a cell attached to the surface and covering both a stimulation and recording electrode will increase the cross-electrode coupling by blocking vertical field lines.

As an example for the effect of cells on cross-electrode impedance, and without wishing to be bound by a particular theory, the inventors recognized that if a cell such as cell 220 as shown in FIG. 2b is adhered to the surface 204 covering some or an entirety of a stimulation electrode 206_0 and a recording electrode 206_1, the cell 220 will increase the cross-electrode coupling by blocking electric field lines 214_1 and 214_2 between the two electrodes from running vertically through the solution 208. As a result, the more vertical field line 214_2 is suppressed and the more field line 214_1' is strengthened compared to in FIG. 2a where no cell is present, resulting in a lower impedance between electrodes 206_0 and 206_1.

On the other hand, if a cell is not adhered to the surface 204, or if a cell such as cell 230 as shown in FIG. 2c is adhered to the surface 204 but disposed outside of and laterally in between the pair of electrodes 206_0, 206_2, the cell may bock electric field lines 214_3 between the pair of electrodes and decrease cross-electrode coupling between electrodes 206_0, 206_2. As a result, cross-electrode impedance may increase between electrodes 206_0, 206_2.

Therefore, the presence of a cell above the electrode array and whether it is adhered to the surface may be detected using cross-electrode impedance measurements. It should be appreciated that a cell that is adhered with a surface may have various degrees of non-zero separation between the outer extent of the cell membrane and the surface. An apparatus according to some aspects of the present application may provide detection for the degree in which the cell is adhered. For example, stronger adhesion will more strongly increase the cross-electrode coupling due to the smaller gap distance along the vertical direction between the cell and the surface of the semiconductor substrate.

The cross-electrode measurements may provide several advantages. For example, such measurements are non-invasive and can be made repeatedly without affecting the cell viability or the electrodes.

In some embodiments and as described above in relation with FIG. 2b, the cross-electrode impedance technique measures an increase in cross-electrode coupling between electrode pairs due to suppression of vertical electric field lines from the presence of a cell, as opposed to techniques that measure a decrease in cross-electrode coupling (or an increase in the measured impedance) due to blocking from the presence of a cell. One advantage for using the increase in cross-electrode coupling as indicator to detect cell presence is that the increase is mainly attributed to electrode pairs that are close to each other, in some cases to nearest neighbor coupling between electrode pairs. Therefore the increase in cross-electrode coupling (or decrease in the measured impedance) can be separated from the total background current flowing through the stimulation electrode to the many remaining electrodes in the electrode array. As a result, signal-to-background ratio and sensitivity of the cell detection can be improved.

In contrast to the cross-electrode impedance technique, the inventors have recognized that simple impedance measured at individual electrodes would fail to detect the presence of cells. In such a measurement on one electrode, the sum of all the return current is measured as the signal for the impedance on the electrode. Namely, such a measurement is an impedance measurement of an electrode only, and are not measuring the change of the electric field in the solution on the electrodes. As a result, the inventors have observed that the impedance of the electrode itself is not sensitive to the presence of a cell even if the cell is culture directly on its surface.

Referring back to FIG. 1a, in some embodiments, a stimulus signal applied by stimulus source circuit 110 to the stimulus electrode 106_1 is a low frequency alternative current (AC) signal, having a frequency of less than 10 kHz, less than 5 kHz, between 0.1 and 5 kHz, or between 0.1 and 2 kHz. The low frequency stimulus signal is selected because the cell membrane acts as a capacitor in parallel with a high resistance, and at high frequency the capacitor impedance would decrease and render the cell highly conductive. The inventors have recognized and appreciated that by measuring cross-electrode current at low frequency can provide high signal contrast for detection of cell adhesion.

An example of the frequency response of cross-electrode impedance measurement is provided in Example 4 below.

Still referring to FIG. 1, the semiconductor substrate 102 may include an active circuitry 116. Active circuitry 116 may include a plurality of stimulation circuits 110 and a plurality of recording circuits 112. In some embodiments, the stimulation circuit 110 may comprise one or more current injectors, one or more voltage sources, or a combination thereof. Some aspects of the active circuitry design are related to current-based stimulators for electrogenic cells and related methods, as disclosed in International Application Publication. No. WO 2019/010343, the disclosure of which is hereby incorporated by reference in its entirety. Some aspects may also be related to electronic circuits for analyzing electrogenic cells and related methods, as disclosed in International Application Publication. No. WO 2019/089495, the disclosure of which is hereby incorporated by reference in its entirety. In some embodiments, the active circuitry may comprise programmable current injectors for performing current-voltage measurements using one or more of the electrodes in the electrode array as working and/or counter electrodes.

In some embodiments, each recording circuit comprises a transimpedance amplifier (TIA) having a switching capacitor as impedance component. The resistance of the impedance component is at least 10 MΩ (megohms), at least 100 MΩ (megohms), or between 10 MΩ and 1 GΩ (gigohm) to provide amplification of a recorded current signal at an input of the TIA, whereas an output of the TIA provides an output voltage that is proportional to the recorded current signal and to a voltage across the impedance component.

Electrodes in the electrode array 106 may be reconfigured using the active circuitry 116 as a stimulation electrode or as a recording electrode. In some embodiments, active circuitry 116 comprises routing and switching components that are programmable to connect a selected electrode of the electrode array 106 to stimulus source circuit 110, to current measuring circuit 112, or to other circuit components to enable different functionalities. Depending on the application, more than one electrode may be configured as a stimulus electrode, and more than one electrode may be recording at the same time. For example, when mapping local cell properties using cross-electrode impedance measurements, typically only one electrode acts as stimulus electrode at a time. In some other embodiments, a subset of one or more electrodes may be selected to act as a stimulus or to apply one or more potentials or currents to initiate an electrochemical reaction at the locations of the selected one or more electrodes. The latter embodiments will be discussed in more detail in the sections below regarding cell-to-cell attachment measurement, patterning, and spatial electrochemical mapping of cells.

In some embodiments, the electrodes may be biased using low impedance sources/returns in the active circuitry. For example, a low output-impedance voltage source may be used to provide a stimulus signal at a stimulus electrode, while a low input-impedance transimpedance amplifier may be provided for current measurement at a recording electrode. In such embodiments, each electrode may be selectively connected to a voltage source for stimulation, to a transimpedance amplifier for current measurement, to a voltage source for a return, or to a transimpedance amplifier for simultaneous stimulation and current measurement. The inventors have appreciated and recognized that the low impedance source/return may facilitate formation of fringing electric field lines in the solution as illustrated in the example in FIG. 1c.

Semiconductor substrate 102 may comprise silicon, and in such embodiments, active circuitry 116 may be an integrated circuit that comprises CMOS components fabricated using standard CMOS processing techniques. The electrode array 106 may be disposed within semiconductor substrate 102, for example as conductors exposed from a surface 104 of the semiconductor substrate 102 that faces the medium 108. In some embodiments, the surface 104 is an insulative surface that provides mechanical support and electrical isolation to the electrode array 106 while also providing a suitable surface for cells to grow. While FIG. 1a shows that the electrode array 106 is partially embedded in the semiconductor substrate 102, such an arrangement is an illustrative example only and not a requirement. In some embodiments, the top surfaces of electrodes in electrode array 106 may be above, aligned vertically with, or below the surface 104 of the semiconductor substrate 102. Additionally or alternatively, the top surfaces of the electrodes may have a passivation layer or functionalization layer. In some embodiments, holes may be patterned in the passivation or functionalization layer on top of the electrodes to expose the conductive surfaces of the electrodes to the medium.

It should be appreciated that semiconductor substrate 102 may be any substrate fabricated using semiconductor processing techniques, and not limited to a silicon wafer. For example, semiconductor substrate 102 may comprise group IV semiconductor, III-V semiconductor, II-V semiconductor, $sp^2$ hybridized carbon material, chalcogenide, metal, metallic compound, oxide, nitride, silicide, polymer material, or combinations thereof. Semiconductor substrate 102 may be a unitary component, or a composite of multiple components. Components in the semiconductor substrate 102 may comprise an active circuit layer, a wiring layer, a redistribution layer, a circuit board, or combinations thereof. Component layers in the semiconductor substrate may be formed in the addition process during CMOS processing, or be formed separately and bonded to each other using packaging techniques known in the field. Conductors are provided in the semiconductor substrate 102 that interconnects active circuitry 116 with the electrode array 106. In some embodiments, connection points are provided at a bottom surface of the semiconductor substrate for electrically interfacing components within the semiconductor substrate with processing unit 120. Electrical connection between processing unit 120 and the semiconductor substrate 102 may be provided via any suitable way, such as but not limited to controlled collapse chip connection or flip chip bonding, wire bonding, flexible cables, or wireless communication.

Referring back to FIG. 1a. In some embodiments, apparatus 100 may be operated to perform a method, such as mapping or performing selective electrochemistry. The operation of the apparatus 100 may be under program control. In some embodiments, processing unit 120 in apparatus 100 may comprise a computer 20 with storage media 21, memory 23, and processor 25, and such processing may be performed in computer 20 or any other computing device. Storage media 21 and memory 23 may be any suitable non-transitory computer-readable medium, such as, for example and not limited to a computer memory, compact discs, optical discs, magnetic tapes, flash memories, circuit configurations in Field Programmable Gate Arrays (FPGAs) or other semiconductor devices, or other tangible computer storage medium. In some embodiments, storage media 21 may be non-volatile storage and memory 23 may be volatile storage. Computer-executable instructions may be loaded from storage media 21 to memory 23 before execution by processor 25 to perform some or all of the methods as described throughout the present disclosure. However, a distinction between storage media 21 and memory 23 is not critical and either or both may be present in some embodiments.

Processor 25 may be any suitable processing device, such as, for example and not limited to, one or more processors, a central processing unit (CPU), digital signal processor (DSP), controller, addressable controller, general or special purpose microprocessor, microcontroller, addressable microprocessor, programmable processor, programmable controller, dedicated processor, dedicated controller, or any other suitable processing device. Some or all components within processing unit 120 may be packaged as a system-on-a-chip (SOC). Moreover, it should be appreciated that FIG. 1a is a schematic representation of a processing unit 120. An actual implementation of a processing unit 120 may have distributed processing. A host computer, for example, may control the overall flow of measurement, mapping and analysis of results.

Turning now to the electrode array 106. In some embodiments, electrode array 106 may be patterned on the surface 104 as part of the semiconductor fabrication process to form the active circuitry 116 within semiconductor substrate 102, and may be conductive pads that comprise metal such as Au or Pt, or alloys thereof. For example, the pads may be formed of Al with plated Au as a top layer. In such embodiments, substrate 110 may additionally comprise conductors that interconnect vertically the exposed electrode array 14 to circuitry within substrate 110.

Electrodes in the electrode array 106 may be arranged on the surface 104 in any suitable arrangement, such as a two-dimensional array with regular pitches along the row and column directions. In some embodiments of the cross-electrode impedance-based mapping, a pitch of the electrode array may be selected to be on the order of or smaller than a size of typical cells such that a cell can cover at least two electrodes to increase coupling between the cell and the at least two electrodes. For example, when the size of cells is about 30 µm, the pitch of the electrode array may be set as less than 30 µm, less than 20 µm, less than 5 µm, or between 1 and 20 µm. Providing a small pitch between electrodes allows a cell to cover two or more electrodes, which permits measuring the cell-to-substrate gap distance via an increase in cross-electrode coupling at the electrodes under the cell.

In some embodiments where the electrode array is fabricated during a CMOS-compatible fabrication process on top of the semiconductor substrate containing CMOS active circuitry, the pitch of the electrode array and size of each electrode may be selected by taking into consideration the pitch and density of the CMOS active circuitry. For example, in some embodiments at least 8, at least 10, or at least 4000 recording circuits may be provided within the semiconductor substrate, and the electrode array may have at least 1000, or at least 4000, or at least 1,000,000 electrodes. In such embodiments, each electrode may have a lateral dimension of no more than 10 µm, or no more than 5 µm, such that the overall lateral extent of the electrode array is contained within the surface of the semiconductor substrate. An electrode array according to aspects of the present disclosure may also be referred to as a CMOS microelectrode array (MEA).

Referring back to FIG. 1, the medium 108 may be a cell culture medium, and may be a solution that comprises any number of chemical and/or biological reagents in addition to cells. While not shown in FIG. 1, medium 108 may be contained in a container disposed on top of the semiconductor substrate 102. In some embodiments, the container may be a well of a multiple-well plate attached to the semiconductor substrate, with one or more wells having an open bottom exposing contents of the well to the semiconductor substrate. The semiconductor substrate may comprise more than one electrode arrays, such that electric assessment in multiple wells may be conducted in parallel.

CMOS-compatible, wafer-scale, multi-well platform that can be used for biomedical or other applications, and methods to operate the same. In some applications, circuitry is provided underneath a multiple-well array to electrically interface with electrodes in the wells. The platform may sometimes be referred to as a CMOS-Multiwell Platform. The inventors have recognized and appreciated that to interface with electrodes in a large array, circuitry may be fabricated on a single silicon (Si) wafer having a dimension that is at least the same or larger than that of the multiple-well array. According to one aspect of the present disclosure, standard CMOS fabrication processes such as those known to be used in a standard semiconductor foundry may be used, e.g., without expensive customization for complex fabrication procedures, and thus the production cost can be lowered in some cases. The CMOS-Multiwell Platform according to some aspects of this disclosure can be used in applications including electrophysiology studies and general cell assessment using electrical methods, and/or in a high throughput format (e.g. 24-, 96-, and 384-well plate formats).

In some embodiments, the Si wafer is part of a semiconductor device, and has an array of reticle areas, with some or all of the reticle areas having a plurality of circuitry of a same design. The inventors have recognized and appreciated that during manufacturing, reticle areas of a wafer may reuse the same lithographical mask design repeated across the wafer in some cases, thus reducing the cost of tooling and increasing the wafer manufacturing throughput.

According to an aspect, digital and analog circuitry within a reticle area may be arranged to correspond to one or more wells when the multiple-well array is coupled on top of the wafer. Some embodiments can therefore provide a wafer-scale integration of electrical interface with a multiple-well array by using a manufacturing method that does not dice the wafer and/or is compatible with standard using standard CMOS-compatible techniques to reduce manufacturing cost.

One aspect of the present disclosure is directed to a technique of mapping the spatial distribution and dimensions of cells using cross-electrode impedance measurements. The mapping may additionally represent a property of individual cells such as adhesion to the surface of a semiconductor substrate. In some embodiments, because cell presence is primarily reflected locally in cross-electrode coupling between a stimulus electrode and nearby recording electrodes, mapping is performed by first choosing an individual electrode as stimulus electrode, and measuring a set of cross-electrode impedance data against other electrodes at locations throughout the electrode array. Subsequently, a different electrode is chosen as stimulus electrode, and a new set of cross-electrode impedance data is measured. The cross-electrode measurements are repeated by sequentially setting electrodes in the electrode array to apply a stimulus signal, and the corresponding set of measurement cross-electrode impedance data may then be processed to generate a value that indicates for each location of the stimulus electrode, whether there is a presence of a cell, or a strength of a cell property. The processed values may then be combined to form a map across the area of the electrode array. In some embodiments, "electro-chemical imaging" of live-cell cultures are demonstrated by high-resolution in situ impedance and electrochemical measurement. Some embodiments are directed to using CMOS-MEAs to perform label-free and non-invasive tracking of cell growth dynamics and accurate measurements of cell-substrate attachment, cell-cell adhesion, and metabolic state.

Another aspect is directed to providing spatially positioned electrochemical reactions using a patterned electrode array. With a selected number of electrodes in the electrode array, active circuitry in the semiconductor substrate may apply potentials to initiate an electrochemical reaction in the solution regions directly above the selected electrodes. As a result, electrochemistry can be performed selectively at a programmed spatial pattern, based on the size, shape and distribution of the selected electrodes on the surface of the semiconductor substrate.

In some embodiments, spatially programmed electrochemistry may be used to perform cell patterning. For example, cells adhered to an electrode may be selectively removed from the electrode surface by electrochemically generate small gas bubbles on the electrode.

In some embodiments, an array of electrochemical electrodes may be used to spatially map analyte concentrations as measured using active circuitry in the semiconductor substrate. One application is an electrochemical mapping of solutions using redox electrochemistry.

The following applications are each incorporated herein by references in their entireties: U.S. Provisional Patent Application Ser. No. 63/040,439, filed Jun. 17, 2020, by Park, et al.; U.S. Provisional Patent Application Ser. No. 63/040,424, filed Jun. 17, 2020, by Ham, et al.; and U.S. Provisional Patent Application Ser. No. 63/040,412, filed Jun. 17, 2020, by Ham, et al. In addition, the following are each incorporated herein by references in their entireties: a PCT patent application, filed on Jun. 16, 2021, entitled "Complementary Metal-Oxide-Semiconductor (CMOS) Multi-Well Apparatus for Electrical Cell Assessment" and a PCT patent application, filed on Jun. 16, 2021, entitled "Apparatuses for Cell Mapping Via Impedance Measurements and Methods to Operate the Same."

The following examples are intended to illustrate certain embodiments of the present invention, but do not exemplify the full scope of the invention.

Example 1: Real-Time Cell Measurements Using a CMOS Microelectrode Array (MEA) and Imaging System This example describes electrical imaging of three parameters useful for live-cell assessment (FIG. 23a): cell-substrate impedance, Zs (reflecting cell attachment and cell-substrate adhesion), transepithelial impedance, Zte, (reflecting cell-cell adhesion and the integrity and barrier function of the cell monolayer), and extracellular redox potential, Vredox (reflective of the cellular metabolic state and respiration).

In this example, a custom designed CMOS IC is used that parallelizes impedance and electrochemical capabilities across a 64×64=4,096 array of electrodes (FIG. 23b-d). A fluidic well is packaged on top of the chip to culture cells and is mounted below a top-down fluorescence microscope for simultaneous optical and electrical measurements (FIG. 23b). The array of electrodes sits at the center of the device, consisting of 8 µm diameter Pt electrodes spaced at a 20 µm pitch for single- or few-cell resolution (e.g. MDCK cells in FIG. 23c), and results in a total sensing area of 1.26×1.26 $mm^2$. The remainder of the surface is insulated with silicon nitride which behaviors similar to glass culture plates. No difference is observed in growth or morphology for cells cultured on the devices in comparison to traditional culture plates. For long-term measurements, an integrated temperature sensor and heater regulate the cells to 35-37° C. and a mini-incubation chamber is placed over the device to regulate $CO_2$ to 5%.

Each electrode in the array is connected to its own pixel circuit (FIG. 23d) which is highly configurable and programmed via a digital interface. The pixel circuit comprises an operational amplifier which can be configured as a buffer for electrode voltage, Ve, measurement, or as a transimpedance amplifier for electrode current, Ie, measurement. Some aspects of the pixel circuit configuration are related to current-based stimulators for electrogenic cells and related methods, as disclosed in International Application Publication. No. WO 2019/010343, the disclosure of which is hereby incorporated by reference in its entirety. Some aspects may also be related to electronic circuits for analyzing electrogenic cells and related methods, as disclosed in International Application Publication. No. WO 2019/089495, the disclosure of which is hereby incorporated by reference in its entirety.

FIG. 23a are schematic diagrams that illustrate three cell parameters that are electrically measured using a complementary metal-oxide-semiconductor (CMOS) integrated circuit (IC) for live-cell assessment: cell attachment via a cell-substrate impedance, $Z_s$, cell-cell adhesion via a transepithelial impedance, $Z_{te}$, and the metabolic state via the extracellular redox potential, $V_{redox}$. Each measurement is non-invasive and fast (<1 min), allowing the measurements to be repeated sequentially every 5~10 min for real-time investigations. FIG. 23b is a picture showing that a fluorescent microscope can be paired with the packaged CMOS IC for simultaneous optical and electrical cell measurement. A reference electrode, Pt (shown) or Ag/AgCl, can be also be used in this example. FIG. 23c is a colorized fluorescent image of Madin-Darby Canine Kidney (MDCK) epithelial cells cultured on top of the CMOS electrode array. The 64×64=4,096 circular 8 μm diameter platinum electrodes are spaced at a 20 μm pitch. Platinum black (PtB) can be electrodeposited onto the electrodes to lower the electrode impedance for higher signal-to-noise $Z_{te}$ measurement. FIG. 23d is a circuit diagram of an exemplary circuit for an electrode in the electrode array. Each of the 4,096 electrodes is connected its own peripheral circuit via a shielded routing (~1-10 mm). The op-amp based circuit can be configured to apply a voltage via Vs and measure a current via a feedback resistor $R_f$ (~100 MΩ), or to apply a current via Is and buffer/measure the electrode voltage, $V_e$. The output of the op-amp, $V_{amp}$, is routed off-chip for analog-to-digital conversion. The switches are digitally programed using a real-time software interface.

In accordance with some aspects, the high channel count (4,096), parallel current and open-circuit potential measurements featured in the measurement techniques in this example provide unique advantages over other MEA devices. For example, measurements as described in this example are prevented in MEA devices that measure the electrode capacitance, voltage with high-pass filters to block DC signals, or current with a small number of channels (<32).

Example 1A: Cell Mapping Using Distribution of Max Current

This example describes a technique of mapping cells using a CMOS electrode array which contains a 64×64 array of 4,096 platinum electrodes at a 20 μm pitch.

The inventors have recognized and appreciated that alternating current (AC) impedance measurements between a pair of electrodes can detect cells using the contrast between the insulative cell membrane and conductive culture media. In a classic impedance measurement, solution paths around the cells shunt the measurement and lower detection sensitivity, as the solution contribution of the measured electrode-to-electrode current is far larger than the small change of current due to the cells. The device as disclosed herein improves detection sensitivity by instead measuring a change of electric field distribution due to the cells.

Figures 3A, 3B:
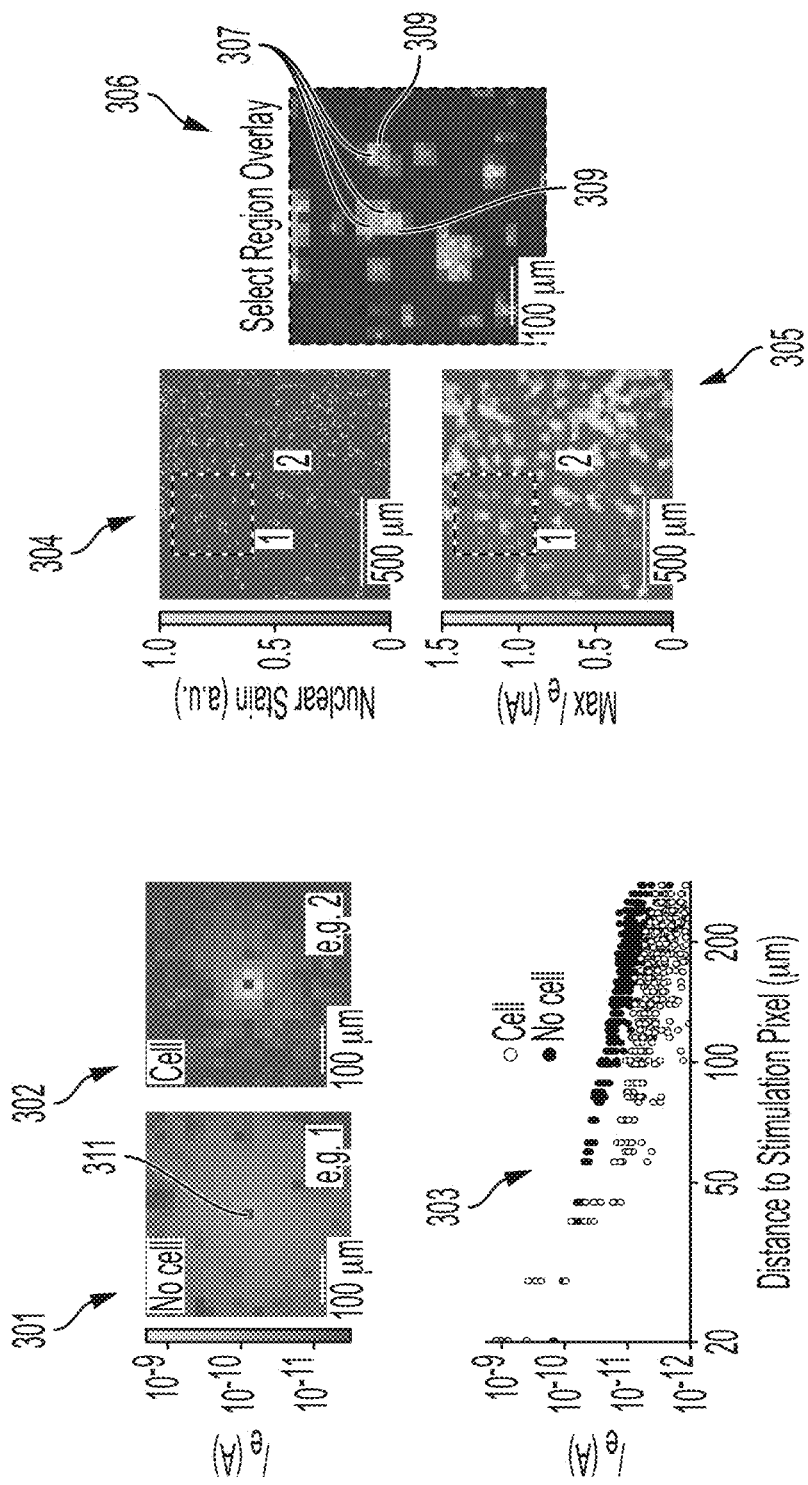
FIGS. 3a and 3b illustrate an example of cell mapping using distribution of max current.

An AC voltage (1.9 kHz frequency, 200 mV amplitude) was applied to one electrode and the resultant AC currents were measured through the remaining 4,095 electrodes using transimpedance amplifiers. The result is illustrated in FIG. 3a, which shows a measured current distribution heat map 301 of the nearest 11×11 recording electrodes to the one stimulus electrode 311 when no cell is present. In heat map 301, each pixel corresponds to a location of an electrode. Each electrode has an electrode location or electrode position that may be expressed in a number of ways, such as but not limited to a coordinate or a pixel number. Heat map 302 is a measured current distribution that is similar to heat map 301, but with a cell on top of the electrode 311. The impedance measurements were done with a 1.9 kHz signal frequency.

The measured cross-electrode current versus distance to stimulation pixel data plot 303 in FIG. 3a shows that in the presence of a cell, the cross-electrode coupling to adjacent electrodes is higher by almost an order of magnitude in comparison to electrodes without cells on top.

In this example, a fluorescent nuclei MDCK cell line was used for optical confirmation. FIG. 3b shows a fluorescent microscopy image 304 across the entire 64×64 electrode array, where the lighter pixel represents fluorescent signals that indicate presence of cells. To generate a cross-electrode impedance map of the same area as image 304, the stimulation electrode was sequentially scanned across the array. For each given stimulation electrode, cross-electrode current values are measured from the remaining electrodes as recording electrodes. The recorded cross-electrode currents are collected and a maximum value is determined, referred to as a max current value corresponding to the given stimulation electrode. FIG. 3b shows a heat map 305 across the electrode array generated using the max current value (Ie) determined from stimulation electrodes at each pixel location.

FIG. 3b also shows a map 306 that is an overlay of a select region 1 of the nuclei fluorescence signals 307 and the max current signals 309 showing the ability to map the cluster of cells with single-cell resolution. As a result, this example demonstrates that the presence of cells was confirmed using nuclei fluorescent markers with a strong correspondence between the max current map and fluorescent imaging.

The max current value (Ie) determined for each stimulation electrode location using any suitable method based on the set of cross-electrode currents measured from the recording electrodes. The determination may be a simple comparison of absolute arithmetic values of the cross-electrode currents, and may additionally include data processing such as noise filtering, background subtraction, or any suitable signal processing technique known in the field prior to the comparison. Processing and comparison of the current values may be performed after digitization of the measured current values, and using a processing unit such as processing unit 120 as shown in FIG. 1a.

Example 2: High Spatial Resolution Mapping Using Cross-Electrode Currents

This example describes a method to generate an up-scaled map of the cross-electrode coupling that has a higher spatial resolution than the pitch of the electrode array.

Figure 4A:
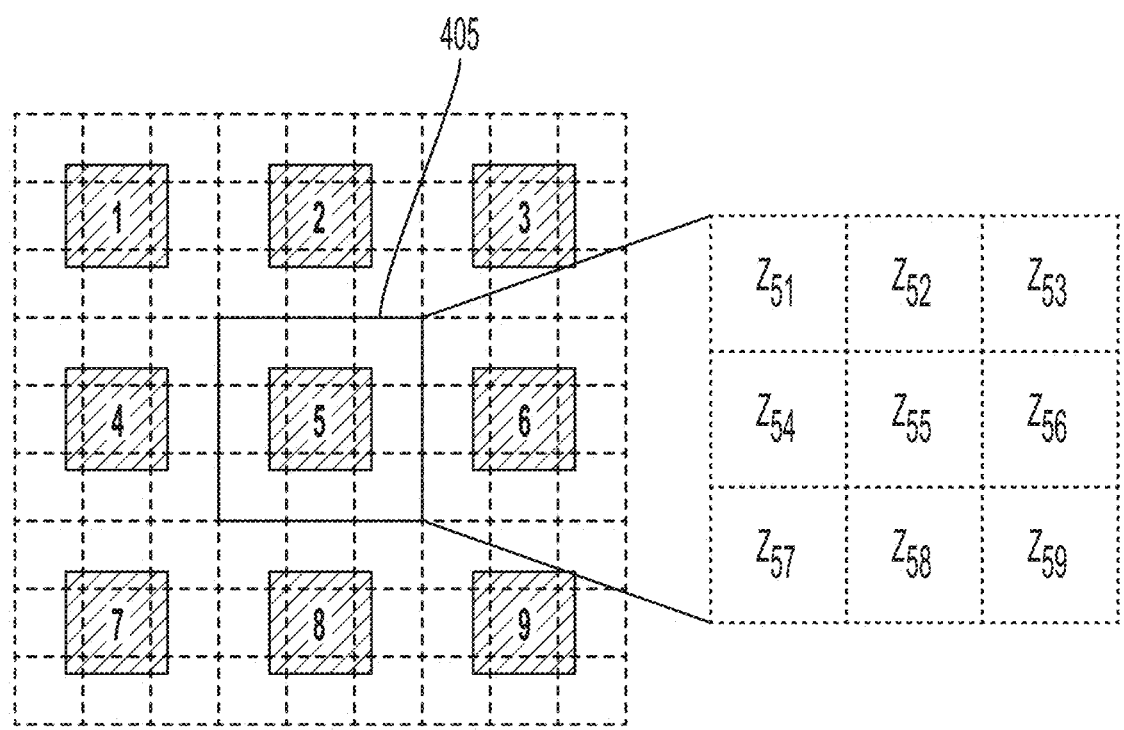
FIG. 4A is a schematic diagram illustrating an example of a high resolution up-scaled mapping using cross-electrode currents.

According to some embodiments, the nearest neighbor cross-electrode measurements may be used for each stimulation electrode. FIG. 4A shows an example of a high resolution up-scaled mapping using a 3×3 impedance grid for each of electrodes 1-9. In some embodiments, electrodes at the edges of the electrode array may be skipped from the up-scaled impedance grid as described below.

Figure 4B:
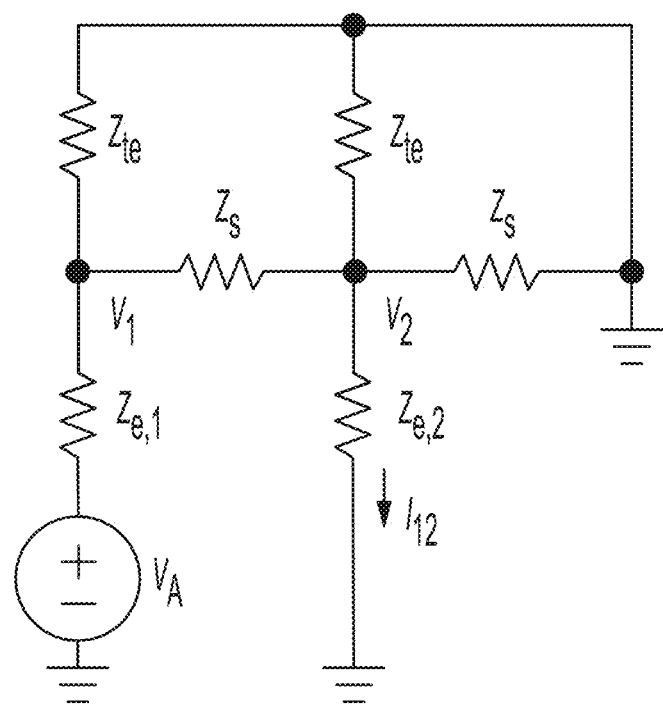
FIG. 4B is a schematic circuit diagram of a cell-circuit model.

FIG. 4B is a schematic circuit model that may be used to calculate the cell-substrate impedance, $Z_s$, and transepithelial impedance, $Z_{te}$, for the application of an AC stimulation voltage, $V_A$, and a measurement of cross electrode current, $I_{12}$. The 3×3 impedance grid is used for the $Z_s$ calculation while a single $Z_{te}$ is extracted for each electrode.

To measure the cell-substrate attachment, a change of cross-electrode field is formed. Instead of applying bias between two electrodes, bias is applied from one electrode to all remaining electrodes. This allows the field lines starting from the stimulation electrode and extending far up into the culture well to terminate on electrodes far away the stimulation. Otherwise, these field lines would need to curl back towards the adjacent electrode, increasing the amount of measured current not related to the immediate cell-electrode interface.

The interface may be modeled using a cross-sectional type model to increase spatial resolution. If we assume $Z_s \ll Z_{te}, Z_{e,1}$, and $Z_{e,2}$, which according to some aspects are found to be valid for most measurement, then:

$$V_2 \approx \frac{1}{2}V_1 \approx \frac{1}{2}V_A \frac{2Z_s}{Z_1 + 2Z_S} \approx V_A \frac{Z_s}{Z_1} \quad \text{(Eq. A1)}$$

The measured cross electrode current can also be written and expressed in terms of (Eq. A1), $$I_{12} = \frac{V_2}{Z_2} \approx V_A \frac{Z_s}{Z_1 Z_2} \quad \text{(Eq. A2)}$$

To determine $Z_{e,1}$ and $Z_{e,2}$, the sum of the measured current across the array is used when the stimulus is applied to an electrode n, $$Z_{e,n} = \frac{V_A}{I_n} \quad \text{(Eq. A3)}$$

$Z_s$ can then be solved for from (A3) and (A2), $$Z_S = V_A \frac{I_{12}}{I_1 I_2} \quad \text{(Eq. A4)}$$

which uses all measured currents.

To generate a high-spatial map of the $Z_s$, nearest neighbor cross-electrode measurements were used for each stimulation electrode: a 3×3 grid is used for each electrode (except those at the edges of the electrode array). See FIG. 4A. This creates an overall $Z_s$ image of 190×190 pixels (in comparison to the 64×64 electrodes in the array).

In the example shown in FIG. 4A, each of the 9 pixels in the 3×3 grid 405 for the center electrode 5 is filled in using normalized impedance values Z based on the measured currents to its nearest neighboring electrodes. Each normalized impedance value Z is calculated as, $$Z_{52} = V_{AC}\frac{I_{52}}{I_5 I_2}, Z_{54} = V_{AC}\frac{I_{54}}{I_5 I_4}, Z_{56} = V_{AC}\frac{I_{56}}{I_5 I_6}, Z_{58} = V_{AC}\frac{I_{58}}{I_5 I_8} \quad \text{(Eq. 1)}$$

where $V_{AC}$ is the amplitude of the applied AC voltage, $I_{xy}$ is the magnitude of the AC current measured by electrode y when the AC signal is applied to electrode x, and $I_x$ [$I_y$] is the sum of the magnitude of the AC currents measured by all other electrodes when the AC signal is applied to electrode x [y]. The edge normalized impedance values are then calculated as, $$Z_{51} = \frac{V_{AC}}{\sqrt{2}}\frac{I_{51}}{I_5 I_1}, Z_{53} = \frac{V_{AC}}{\sqrt{2}}\frac{I_{53}}{I_5 I_3}, Z_{57} = \frac{V_{AC}}{\sqrt{2}}\frac{I_{57}}{I_5 I_7}, Z_{59} = \frac{V_{AC}}{\sqrt{2}}\frac{I_{59}}{I_5 I_9} \quad \text{(Eq. 2)}$$

where the square root of 2 was determined to normalize the difference in distance between the edge and corner electrodes. The center normalized impedance value is then determined as, $$Z_{55} = \text{median}(Z_{52}, Z_{54}, Z_{56}, Z_{58}) \quad \text{(Eq. 3)}$$

The use of the cross-electrode currents not only increases the effective spatial resolution in comparison to using the max of the current distribution but it also allows for unadhered cells, which cause a decrease in the cross-electrode current, to be mapped.

Figure 5B:
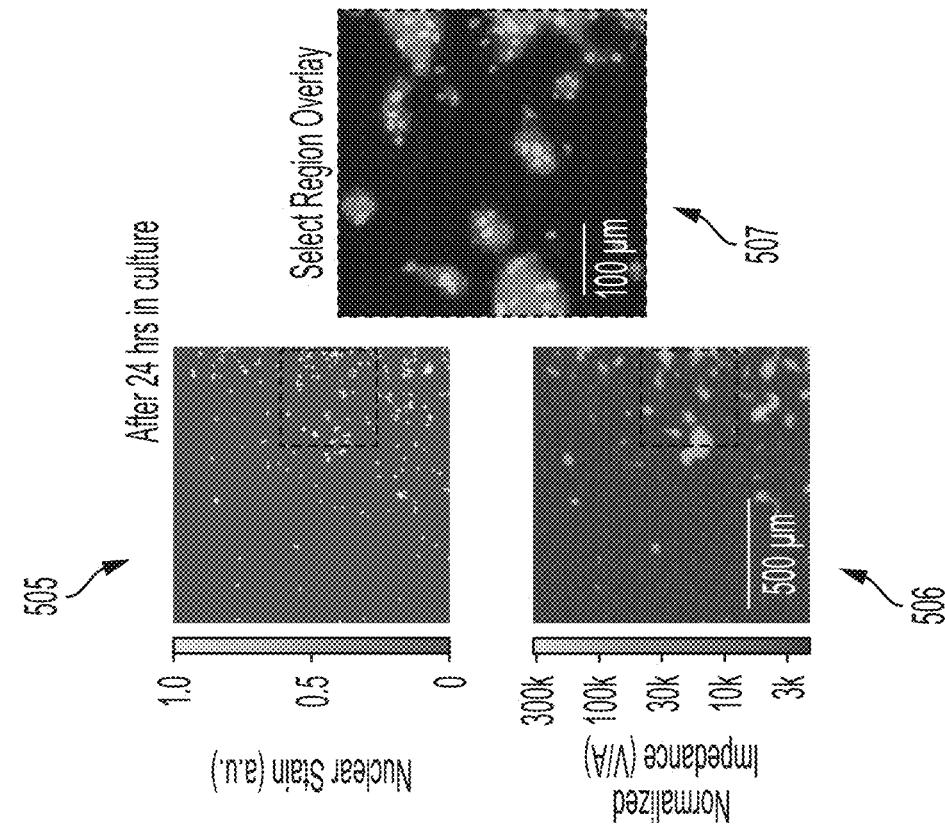
FIGS. 5a and 5b illustrate an example of up-scaled cross-electrode impedance mapping in comparison with a fluorescent microscopy image.
Figure 5A:
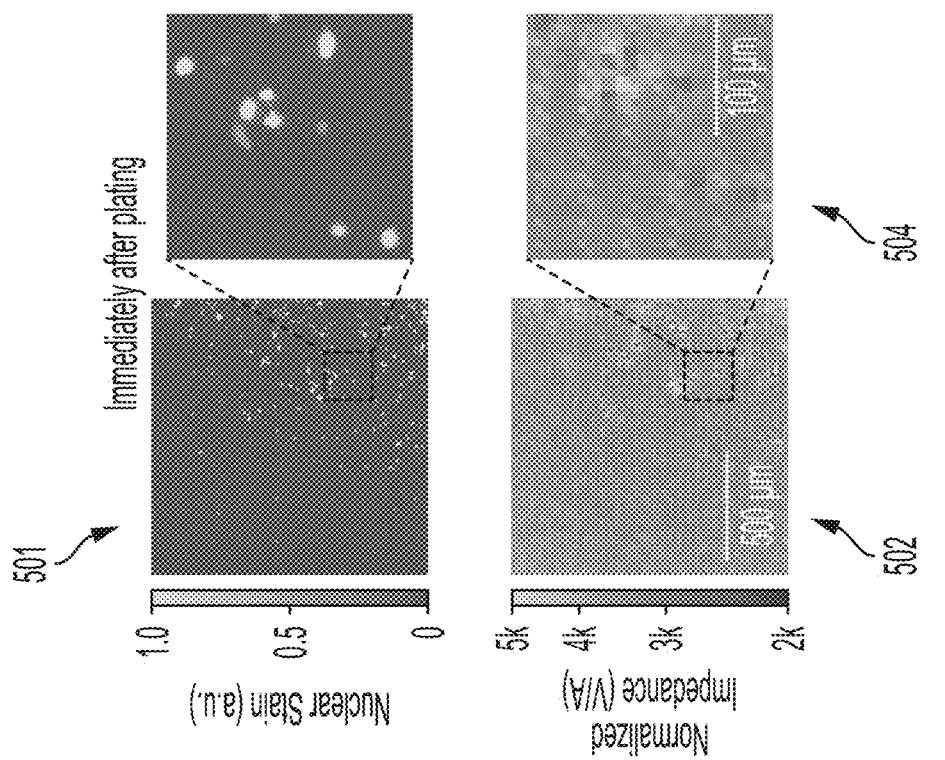

FIGS. 5a and 5b illustrate an example of up-scaled cross-electrode impedance mapping in comparison with a fluorescent microscopy image. FIG. 5a shows a fluorescent microscopy image 501 across the electrode array and a heat map plot 502 of the normalized cross-electrode impedance of a cell culture immediately following plating. The enlarged map 504 of a portion of heat map 502 shows a decrease in the cross-electrode normalized cell-substrate impedance Zs for the unadhered cells with single-cell resolution. The mapping immediately following a plating of cells such that the cells are not adhered shows smaller normalized impedance values where the cells are in comparison to non-covered electrodes.

FIG. 5b shows a fluorescent microscope image 505 and a cross-electrode impedance map 506 after 24 hours of culture. FIG. 5b also shows an enlarged map 507 that is an overlay of fluorescent microscope image and cross-electrode impedance map at a select region. The results show that many of the cells have adhered to the surface, causing a drastic increase in the normalized cross-electrode impedance.

Example 3: Quantifying Cell Adhesion

This example describes a method using cross-electrode impedance mapping to quantify cell adhesion.

Ethylenediaminetetraacetic acid (EDTA) is applied to the cells. EDTA is a calcium chelator that removes $Ca^{2+}$ needed for integrin proteins to maintain cell adhesion. With EDTA applied, the cells quickly detach over the time course of ~50 min. The EDTA is then washed out by adding normal culture media, where the cells re-attach over the time course of ~200 min.

Figure 6C:
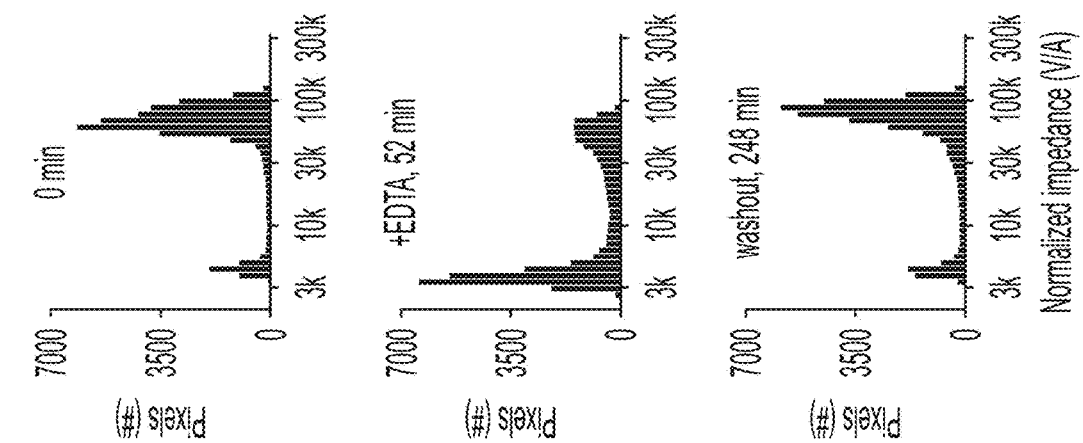
FIGS. 6a-6c illustrate an example using cross-electrode impedance mapping to quantify cell adhesion.
Figure 6A:
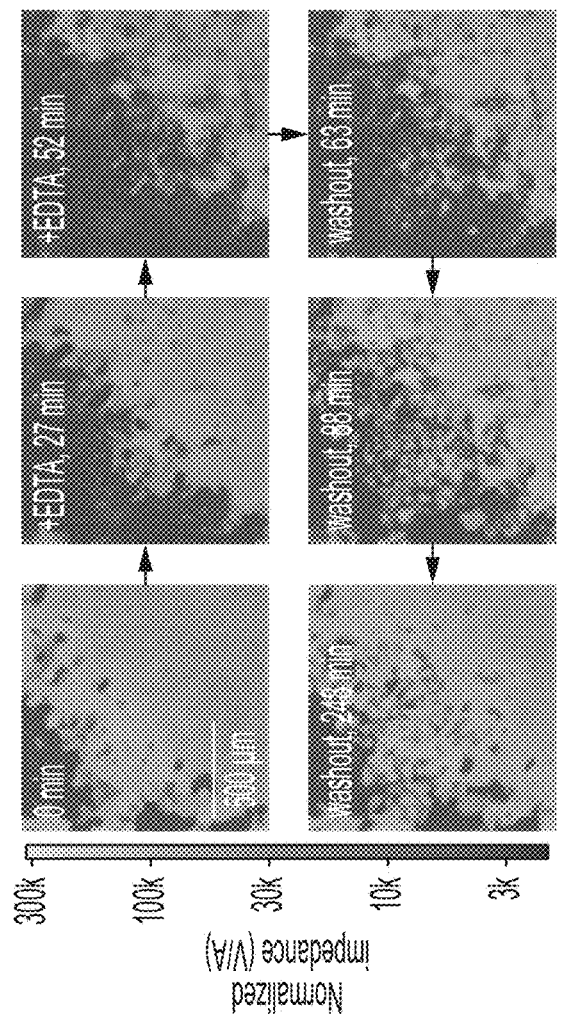

The detachment and reattachment of the cells is captured with high spatial and time resolution using cross-electrode impedance mapping, as demonstrated in FIG. 6a, which shows a series of normalized impedance maps over time of MDCK cells with a 5 mM EDTA application at t=~5 min and a washout at t=~55 min.

Figure 6B:
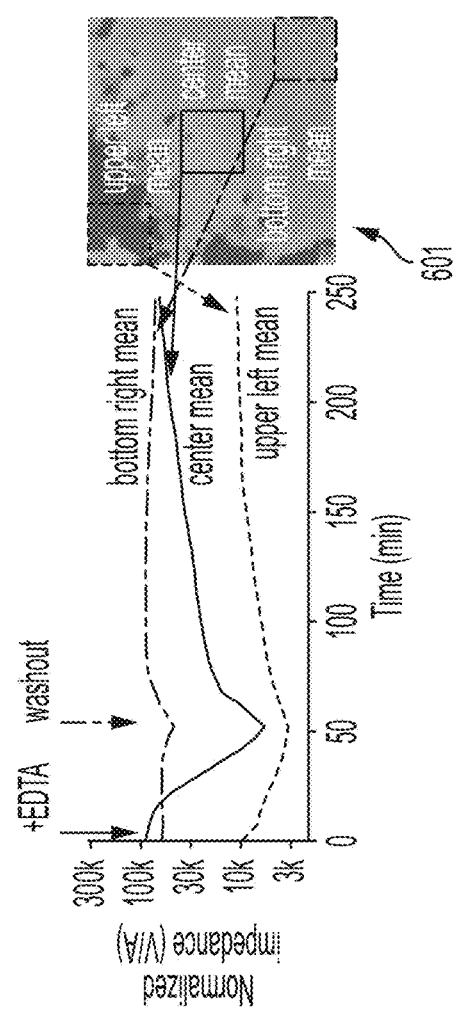

FIG. 6b is a data plot showing mean normalized impedances for different regions of the cell culture over time as specified in the map 601. FIG. 6cc are histograms of the normalized impedance values before, during, and after a washout of EDTA across the array.

Figure 7:
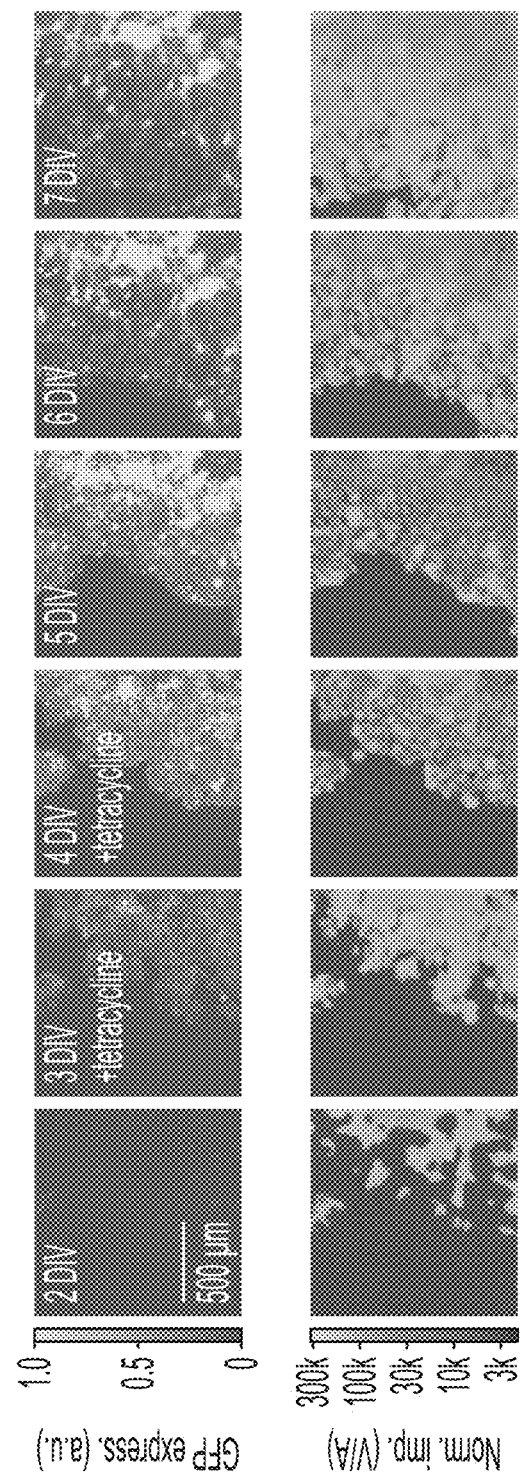
FIG. 7 is a series of fluorescent microscope images and normalized cross-electrode impedance maps.

To show a biologically relevant example of quantifying cell adhesion, a genetically modified MDCK cell line was measured wherein tetracycline was used to turn on and off a RasV12 and GFP gene. The result is shown in FIG. 7. FIG. 7 is a series of fluorescent microscope images and normalized cross-electrode impedance maps of MDCK cells over 7 days of culture in vitro (DIV). Tetracycline is added after the 2 DIV measurement to turn on the gene RasV12 which is related to cancer, the gene also expresses GFP such that gene expression can be imaged. The tetracycline is then removed after the 4 DIV measurement to turn off the gene expression. The cells are shown to be less adherent to the surface when the RasV12 gene is expressed and returns to normal after it is turned off.

Figure 8A:
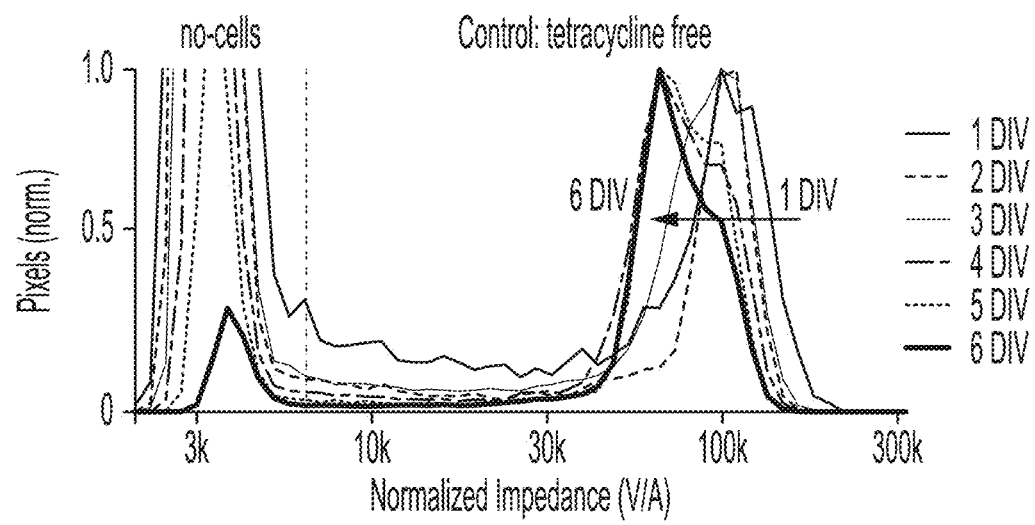
FIG. 8a is a normalized impedance histogram of a control measurement without the tetracycline added.
Figure 8B:
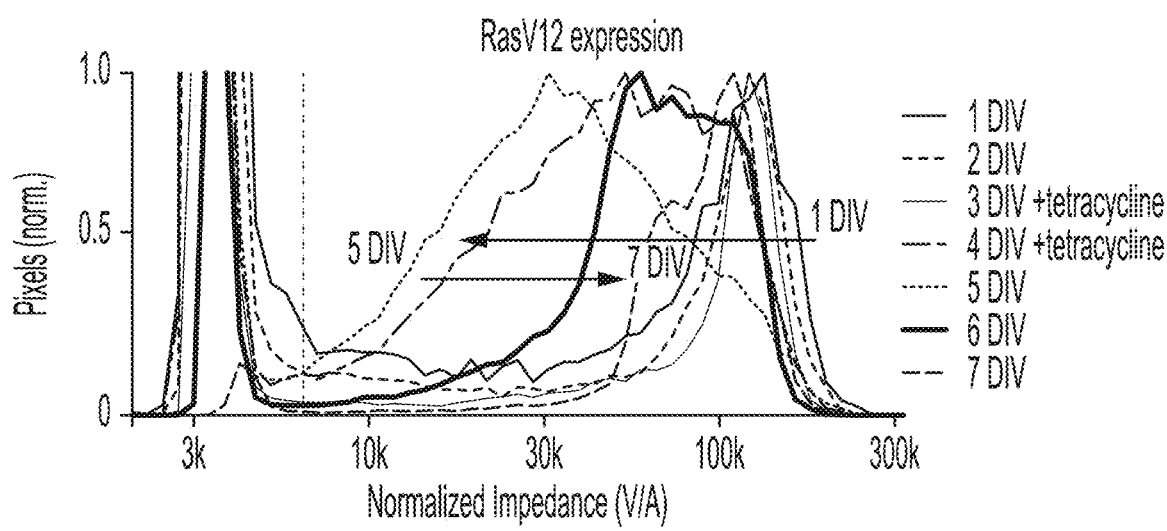
FIG. 8b is a normalized impedance histogram of MDCK cells over 6-7 days of culture in vitro (DIV)

RasV12 is an oncogene and has been known to increase cell metabolism and decrease cell adhesion when strongly expressed, which together cause cancer-like cell growth and tumors. Originally, tetracycline was kept out of the media and the cells were adhered as normal. When tetracycline was introduced, the genes were expressed causing an increase in GFP and a decrease in cell adhesion. Removal of tetracycline then reversed the cell adhesion to cause the cells to more strongly adhere while also decreasing overall GFP expression; some portions of the cell culture did not turn off as strongly as others. The effects on cell adhesion were quantitatively compared to a control culture which did not have tetracycline introduced, as shown in FIG. 8. FIG. 8b is a normalized impedance histogram of MDCK cells over 6-7 days of culture in vitro (DIV). Tetracycline is added after the 2 DIV measurement to turn on the gene RasV12 which is related to cancer. FIG. 8a is a normalized impedance histogram of a control measurement without the tetracycline added. The histograms have been normalized to the max pixel number above the no-cell impedance values of ~8 kΩ. The cell adhesion was reduced in comparison to the control, which showed a smaller decreasing trend over time.

Example 4: Frequency Response

This example describes the effect of frequency used in the cross-electrode impedance measurements.

Figure 9:
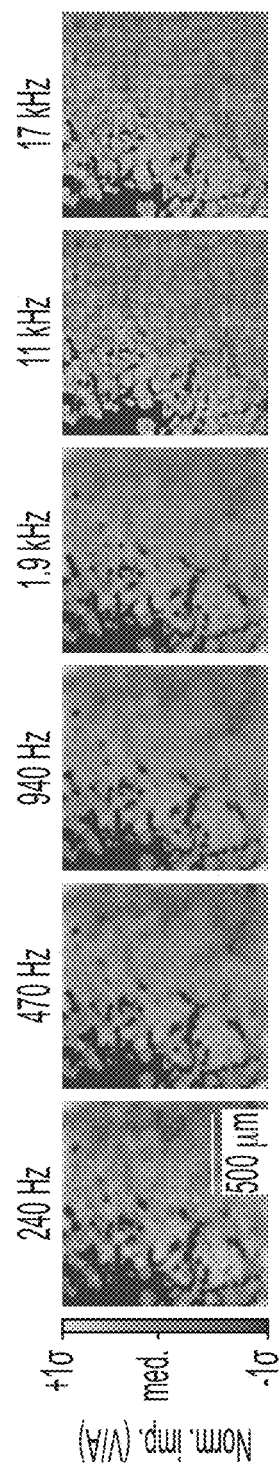
FIG. 9 shows a series of normalized cross-electrode impedance maps under different frequency stimulus signals.

The frequency of mapping was swept to determine the best frequency for measuring the cell adhesion using cross-electrode impedance mapping. FIG. 9 shows a series of normalized cross-electrode impedance maps under different frequency stimulus signals. The plots are normalized to the median+/−1 standard deviation. The lower frequencies show higher signal contrast which correlates to the optically measured GFP fluorescence as shown in FIG. 7, which indicates that low frequency is better for measuring cell adhesion. The used 1.9 kHz still shows good contrast in comparison to the 240 Hz, but above 10 kHz, the cell sheet looks much more uniform.

Example 5: Cell-to-Cell Adhesion

Figures 10A, 10B:
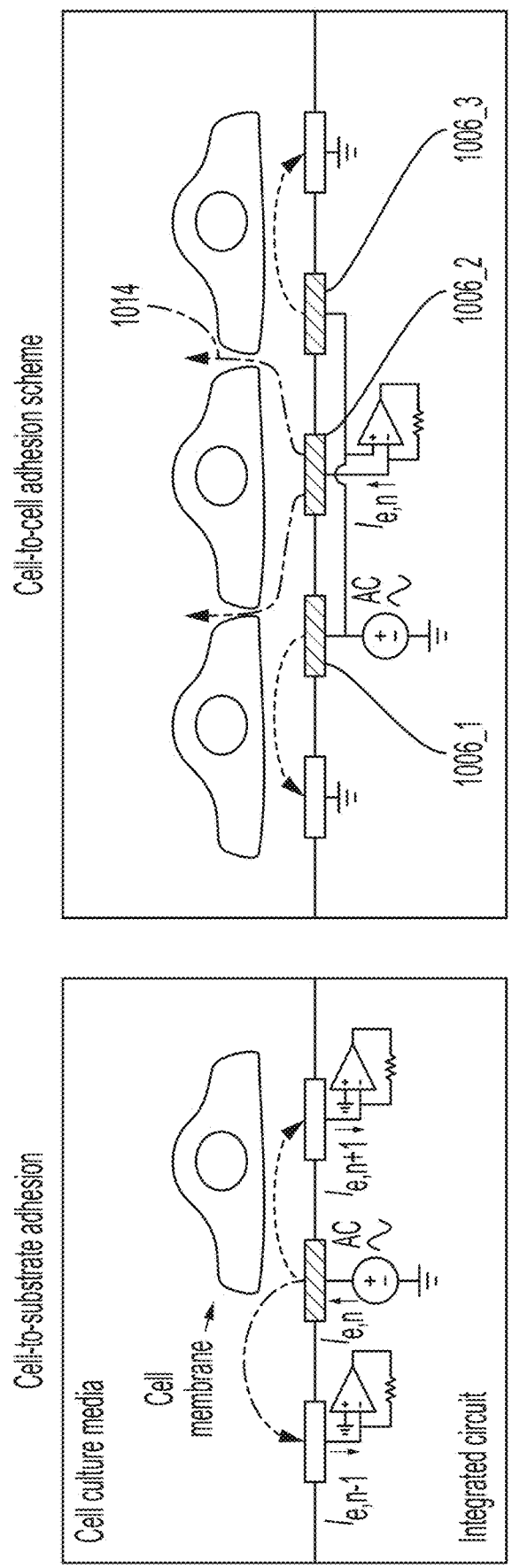
FIG. 10a illustrates an example of mapping cells and their adhesion over time via a cross-electrode impedance measurement.
FIG. 10b illustrates an example of measuring cell-to-cell attachment.

The previous examples are directed to how to map cells and their adhesion over time via a cross-electrode impedance measurement, as depicted in FIG. 10a. In FIG. 10a, an AC voltage is applied to a single electrode and the currents are measured through the remainder of the electrode array using transimpedance amplifiers. The adhesion is mainly a function of the cell-to-substrate attachment and resultant height of the gap.

This example describes a method to measure cell-to-cell attachment, or how well connected the cells are to each other. Cells in culture not only attach to the surface, but also to each other via cell-cell connections. The tightness of these connections defines the permeability of a cell sheet and is important for epithelial tissues which act as barriers of the body surfaces, internal organ linings, and other tissues. In this example, this barrier function is measured by performing a map of the transepithelial impedance, $Z_{te}$. In this way, the cell-cell connectivity could be assessed using electrodes only covered by cells to mitigate any holes while also allowing for spatial heterogeneity assessment.

In this example, the stimulation protocol is modified to measure the vertical field component 1014 as shown in the diagram in FIG. 10b. In FIG. 10b, an electrode 1006_2 and its surrounding electrodes 1006_1, 1006_3 are biased with an AC voltage. A current Ie,n is measured through the center electrode 1006_2. The center electrode 1006_2 will not pass current to surrounding electrodes as they are biased with the same signal, therefore it will only pass current due to the impedance of cell sheet above the electrode. Outside of the center and its surrounding electrodes, the remainder of the array is biased at ground or a reference voltage level to act as a current return. This type of measurement is similar to measuring the transepithelial electrical resistance (TEER), which is measured using two electrodes on opposite sides of a cell culture on a suspended porous membrane. The technique shown in FIG. 10b allows the TEER to be mapped across the cells on top of the electrode array without the need for special suspension. Advantages include fewer cells needed, ability to assess spatial heterogencity, and the ability to combine cell-to-cell and cell-to-substrate adhesion measurement using the same device.

Figures 24A, 24B:
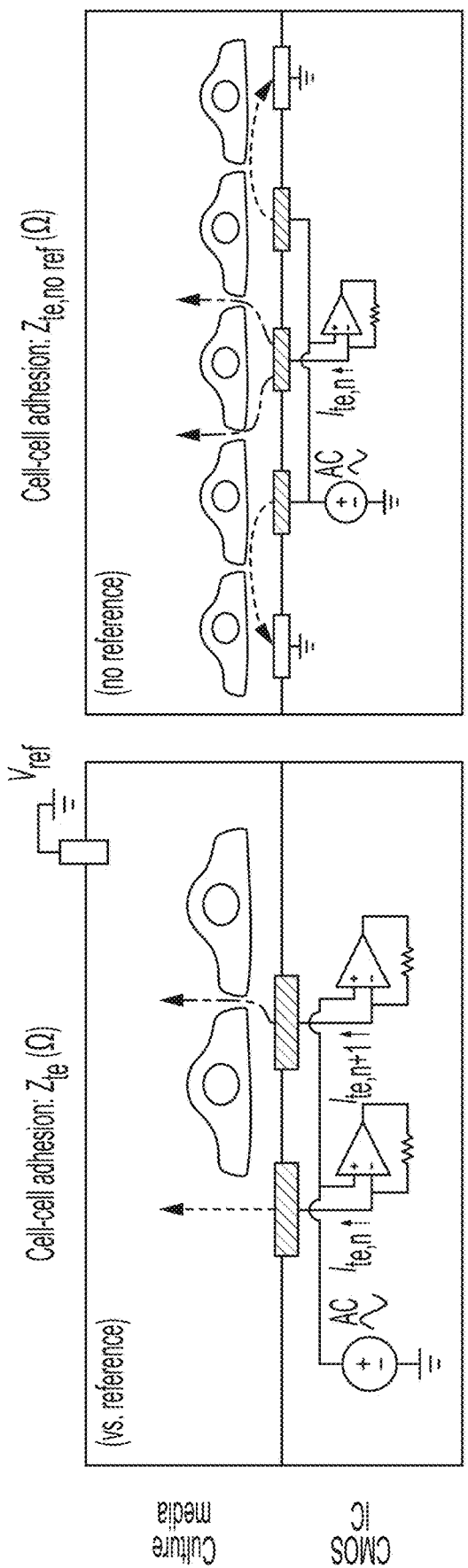
FIG. 24a, 24b are schematic diagrams illustrating some additional schemes of cell-cell connectivity measurements, in accordance with some embodiments.

FIG. 24 includes schematic diagrams illustrating some additional schemes of cell-cell connectivity measurements, in accordance with some embodiments. In FIG. 24, the change of the vertical field above the electrode is measured to best isolate the effects of the cell-cell connections using two circuit configurations: 1) a fast (<1 s/measurement) parallel electrode measurement versus a reference (FIG. 24a), and 2) a slow scanned (40 s/measurement) relative measurement without a reference (FIG. 24b). The fast measurement is ideal for sweeps across multiple frequencies whereas the scanned measurement does not require a reference which helps to make long-term measurements more stable and is more ideal for device miniaturization. For both types of measurements, platinum black (PtB) deposition can be optionally used to lower $Z_e$ by about 5× to improve $Z_{te}$ sensitivity. Experiments across frequency showed that mid-range frequencies of ~2 kHz to 5 kHz were best for assessing cell-cell connectivity.

The calculation of transepithelial impedance Zte using the schemes in FIG. 24 is now discussed below.

To measure cell-to-cell attachment, or how well connected the cells are to each other, we can modify the stimulation protocol to measure the vertical field component in FIGS. 24a, 24b. Measurements can be made versus a grounded reference (left) by applying an AC voltage to all electrodes with the each transepithelial electrode current, $I_{te,n}$ (n=1, 2, . . . 4096), measured via transimpedance amplifiers (measurement duration of 1 s/frequency). The resultant field distribution is vertically aligned with the connectivity of the cells decreasing the $I_{te}$. A non-reference measurement can be made (right) by applying an AC voltage to an electrode (n) and its neighboring electrodes to create an effective vertical field measurement with the remainder of the electrodes' grounded. To generate a cell map, the applied signal is scanned across the array (40 s per scan/frequency).

In the parallel scheme in FIG. 24a, an AC voltage is applied to each electrode versus a reference with each electrode's current, $I_{te,n}$, measured, creating a vertical field in solution (the peripheral electrodes would also have a fringing field for low frequencies. Due to current then needing to go through the cell sheet, the magnitude of the current will be proportional to the transepithelial impedance, $Z_{te}$. A second scanned scheme, FIG. 24b, biases an electrode and its surrounding electrodes with an AC voltage and measures the current only through the center electrode. The center electrode will not pass current to surrounding electrodes as they are biased with the same signal, therefore it will only pass current due to the impedance of cell sheet above the electrode. Outside of the center and its surrounding electrodes, the remainder of the array is biased at ground to act as a current return.

In either case, the measured vertical current $I_{te,n}$ can be expressed, $$I_{te,n} = \frac{V_A}{Z_{e,n} + Z_{te}} \quad \text{(Eq. A8)}$$

Using (A3), we can then solve for $Z_{te}$, $$Z_{te} = \frac{V_A}{I_{te,n}} - \frac{V_A}{I_n} \quad \text{(Eq. A9)}$$

For measurements, it was determined that mid-frequencies from ~1-5 kHz are best correlated with the cell-cell connectivity (see also Example 15, below). For the PtB electrodes, $Z_{e,n}$ is then sufficiently smaller than $Z_{te}$ (see also Example 15, below) such that it is estimated that:

$$Z_{te} = \frac{V_A}{I_{te,n}} \quad \text{(Eq. A10)}$$

For $Z_{te}$ experiments with just Pt electrodes, the $I_n$ measurement from the cell-substrate impedance is subtracted. Due to the scanned array measurement to calculate $Z_{te,no\ ref}$ using a 3×3 set of electrodes, the total map generated is 62×62 pixels, as the peripheral electrodes do not have neighboring biased electrodes to create the vertical field. The measurement versus the reference creates a map containing 64×64 pixels.

Example 5A: Metabolic State Mapping Via Extracellular Redox Potential, $V_{redox}$ Beyond impedance measurements, platinum electrodes have been used for both potentiometric sensing of oxygen and extracellular redox monitoring. This example demonstrates that we could use the proximate location of Pt electrodes directly underneath live cells to map the extracellular redox potential, $V_{redox}$, in situ to monitor the redox environment of the cells and even $O_2$ consumption to map out the metabolic state of cell cultures.

Figure 25A:
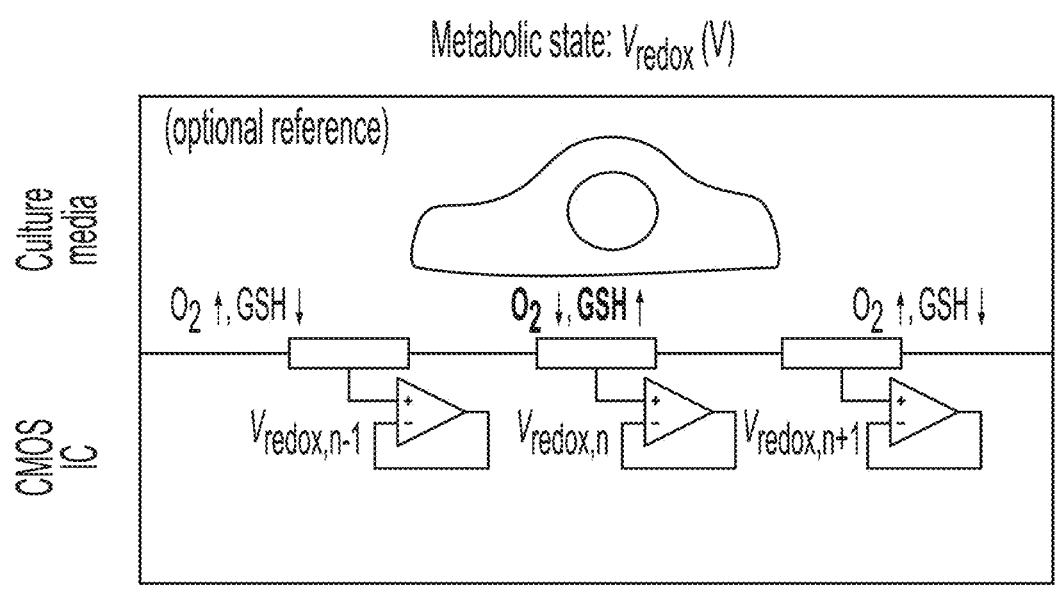
FIG. 25a is a schematic diagram illustrating a pixel amplifier configured as a buffer for metabolic state measurement.

To accomplish the measurement, the pixel amplifier is configured as a buffer, as shown in the schematic diagram in FIG. 25a.

In general, cells use energy arising from the movement of electrons from oxidizable organic molecules (e.g. glucose) to $O_2$ during aerobic metabolism. To help mediate these electron flows, a general reducing environment is created by the thiol-compound glutathione (GSH) which is often considered to be the cellular redox buffer. In simplified terms, the redox potential of the cell is then a balance between $O_2$ pulling the potential up (oxidizing) and GSH pulling the potential down (reducing). The redox environment is not only important for electron transfer, but also for neutralizing harmful reactive oxygen species, cell-cell signaling, and regulating the state of the cell. For example, ranging from negative to positive, the redox potential can determine if a cell is in a state of proliferation, differentiation, apoptosis, or necrosis.

Figures 25B, 25C, 25D:
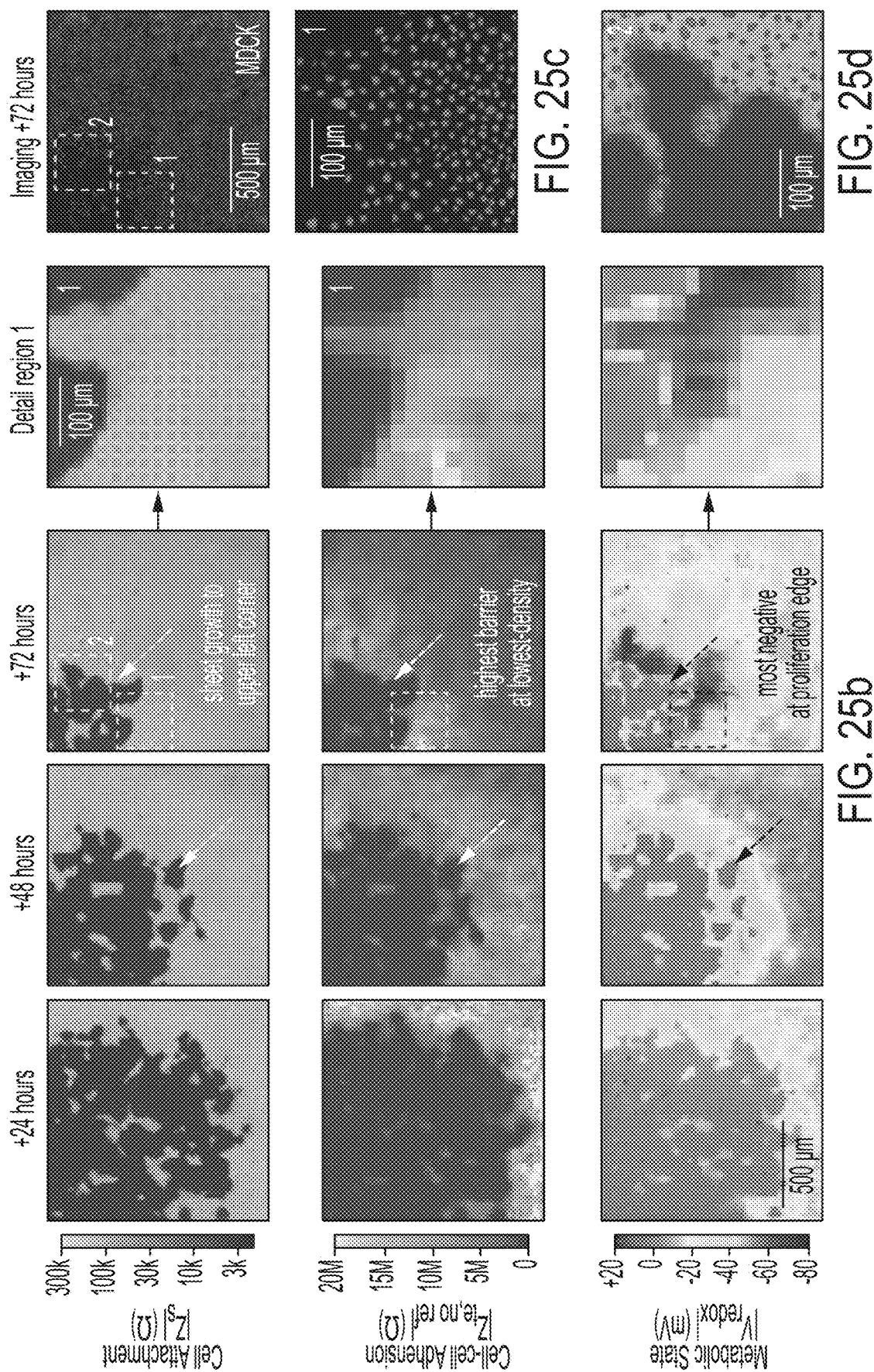
FIG. 25b are a series of data maps showing results of multi-parametric measurements.
FIG. 25c is a pair of nuclei fluorescence images at +72 hours after plating (top) and a detail region 1 comparison (bottom) showing the lowest cell density on the leading edge in comparison to the trailing edge.
FIG. 25d is a composite map showing a detail region 2 overlaying the cell nuclei and cell attachment.

FIG. 25b are a series of data maps showing results of multi-parametric measurements. The measurements are performed at +24, +48, and +72 hours after MDCK cell plating including cell attachment (top), cell-cell adhesion (middle), and metabolic state (bottom). The cells exhibit growth from the bottom right to the upper left corner, where the proliferating leading edge cells proliferating show the most negative $V_{redox}$ in comparison to the more dormant trailing edge. The $Z_{te}$ is highest at the leading edge as well, due to the lowest density of cells, see detail region 1, and therefore the fewest cell-cell connections. FIG. 25c is a pair of nuclei fluorescence images at +72 hours after plating (top) and a detail region 1 comparison (bottom) showing the lowest cell density on the leading edge in comparison to the trailing edge. FIG. 25d is a composite map showing a detail region 2 overlaying the cell nuclei and cell attachment. FIG. 25d shows good spatial correspondence with single-cell resolution.

One goal of this example is to investigate what information the proximate $V_{redox}$ could provide by pairing it with the impedance techniques to monitor cell growth (FIG. 25b). In this example, a negative $V_{redox}$ in the range of 30 mV to 80 mV was observed for electrodes with cells in comparison to electrodes without cells (FIG. 25b). From the detail region comparison, the spatial information of $V_{redox}$ is distinct and different than the cell attachment or cell barrier, where the most negative $V_{redox}$ is at the leading edge and not the lowest density. In general terms, the negative signal could indicate a locally smaller $[O_2]$ or locally higher [GSH] near the cells.

To further explore the $V_{redox}$ signal origin, the $O_2$ dependence was tested via an oxygen purge on a separate MDCK cell culture. Upon the $O_2$ removal, the signal difference between regions with cells and without was eliminated. To complement, the GSH based reducing capacity was tested via an oxidative titration. Ferricyanide, $[Fe(CN)6]^{3-}$, was chosen for the titration due to its previous non-toxic use in cell-cultures and its oxidizing half-cell potential in comparison to the cellular environment. The media showed a 4 μM reducing capacity while the cells had a much larger capacity of >200 μM.

Taken together, these measurements show that the measured $V_{redox}$ is related to both the in situ [$O_2$] and [GSH]-based reducing capacity of the cells. We theorize that with aerobic respiration, the [$O_2$] lowers from its normal dissolved concentration of ~200 M at atmospheric conditions which lowers $V_{redox}$ until it is regulated by the extracellular reducing potential of the cells. Therefore, though it is difficult to quantify oxygen consumption rate with our technique, the $V_{redox}$ measurement of the extracellular redox potential can be useful for monitoring the metabolic state of cells, as it can show both the usage of $O_2$ and the reducing environment of cells. Therefore, the more negative signal on the leading edge of the cell sheet (FIG. 25b) is attributed to respiration combined with a state of proliferation, the most negative redox potential state of a cell.

Example 6: Antibody-Cell Binding

Screening for antibody-cell binding can be low-throughput due the need for either fluorescent tagging of the antibodies, which requires wash steps to remove non-bound fluorescent antibodies, or the need for a special optical measurement such as surface plasmon resonance (SPR). According to one aspect, the cross-electrode impedance technique described herein may offer the ability to measure the antibody-cell binding event through either the cell-to-substrate or cell-to-cell adhesion measurements. With the binding of an antibody on the underside of the cell, the gap distance becomes effectively smaller leading to a decrease in the amount of cross-electrode current measured. Likewise, with antibody binding to the sides of the cells, the cell-to-cell gap distance should also become smaller, leading to a decrease in the amount of vertical current measured. Being able to perform such antibody binding without labels then allows for different antibodies to be added in sequence without the need for wash steps, greatly improving throughput.

Example 7: Cell Patterning Through Electrochemical Gas Generation

Figure 11:
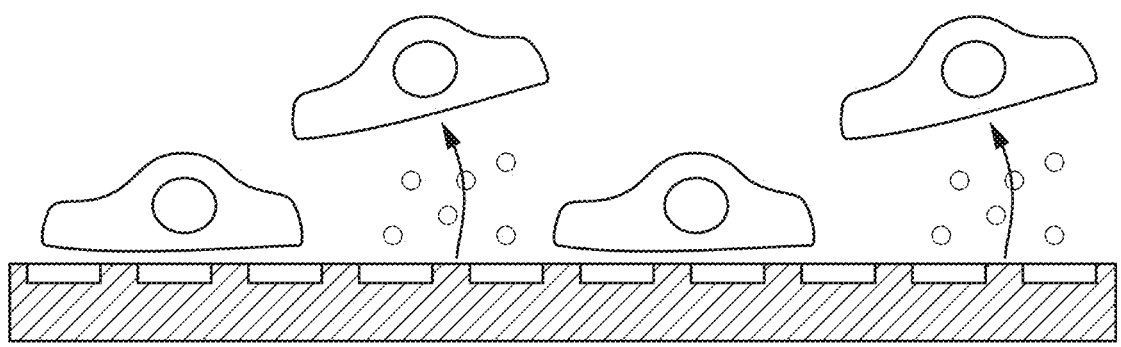
FIG. 11 is a schematic diagram illustrating cell patterning through electrochemical gas generation.

This example describes a method to pattern cells on top of an electrode array. The inventors have recognized and appreciated that small gas bubbles can be electrochemically generated to generate small holes in the cell membrane to kill the cells via depolarization. After death, cells will then detach from the surface, as illustrated in the schematic diagram in FIG. 11. Therefore, by controlling which electrodes generate gas, the cells can be patterned with the spatial resolution of the electrode array.

Without wishing to be bound to a particular theory, the inventors recognized that for most inert electrode materials (platinum, gold, etc.) hydrogen gas can be generated by adjusting the electrode potential below the hydrogen ion/hydrogen gas redox half-cell reduction potential ($E^0$),

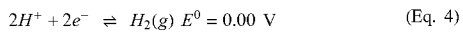
$$2H^+ + 2e^- \rightleftharpoons H_2(g) \; E^0 = 0.00 \text{ V} \quad \text{(Eq. 4)}$$

or oxygen gas can be generated by adjusting the electrode potential above the oxygen gas/water redox potential,

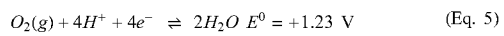
$$O_2(g) + 4H^+ + 4e^- \rightleftharpoons 2H_2O \; E^0 = +1.23 \text{ V} \quad \text{(Eq. 5)}$$

Likewise, as most cell media contain chloride salts, chloride gas may also be generated by adjusting the electrode potential above the chlorine gas/chloride redox potential,

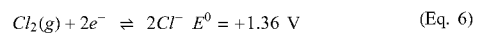
$$Cl_2(g) + 2e^- \rightleftharpoons 2Cl^- \; E^0 = +1.36 \text{ V} \quad \text{(Eq. 6)}$$

Accordingly, cell removal may be performed by selectively applying a pre-determined potential that is above a redox potential for generation of a gas at one or more electrode locations. The potential may be applied, for example by connecting one or more stimulus source circuits 110 in FIG. 1a to the selected electrodes. The potential needs not to be identical across all selected electrodes, and programmable heterogeneity may be used when electrodes are biased differently. The potential may be a potential relative to a potential of a reference electrode in the medium above the electrodes.

For more controllable patterning, an electrode current can be used to set the electron transfer rate and therefore the rate of gas generation. Controlling the rate of gas generation can optimize the selective electrochemical reaction as large bubbles can form on the surface by using too fast of a gas generation rate, blocking the electrodes from solution.

FIG. 13 is a series of diagrams illustrating variations of cell patterning using an electrode array. FIGS. 13a and 13b illustrate embodiments where one or more pre-determined patterning voltages are applied to selected electrodes for patterned removal of a cell by electrochemical gas generation. FIGS. 13c and 13d illustrate embodiments where one or more pre-determined patterning currents are applied to selected electrodes for patterned removal of a cell. FIGS. 13a and 13c illustrate an example of voltage/current patterning with a reference electrode acting as a return. FIGS. 13b and 13d illustrate an example of differential voltage/current patterning using cross-electrode gas generation without using a reference electrode, where one set of electrodes passes a positive current and a second set of electrodes passes a negative current (return).

Example 8: Cell Spatial Patterning and Defining a Co-Culture

This example describes spatial patterning of cells and definition of a co-culture using an electrode array.

Figure 12:
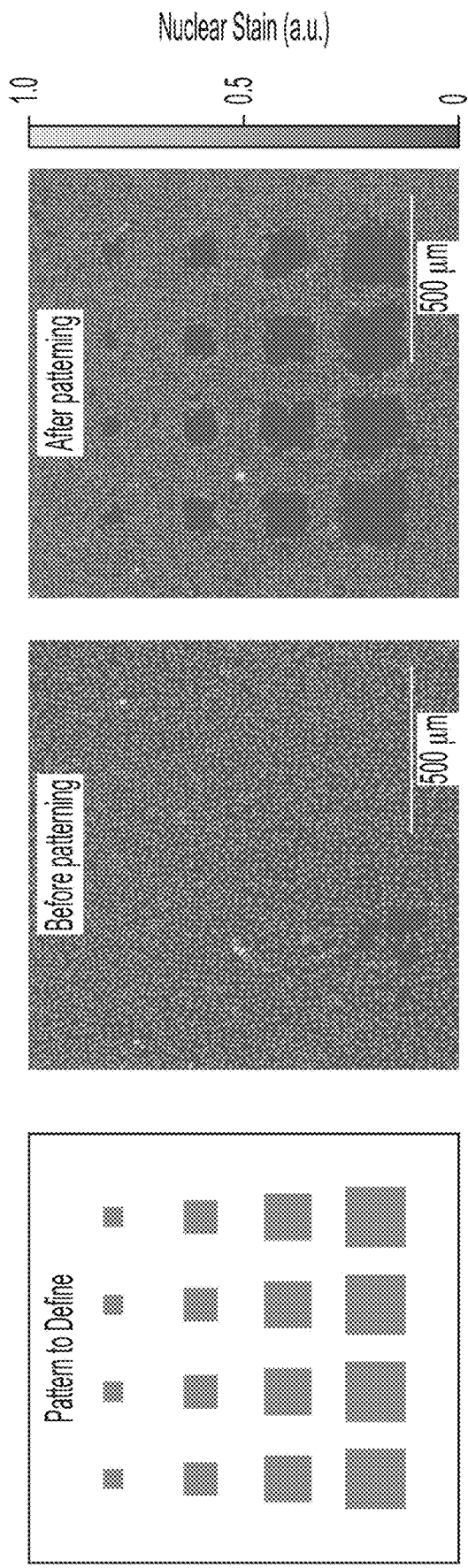
FIG. 12 illustrates an example of cell spatial patterning and defining a co-culture.
Figure 13B:
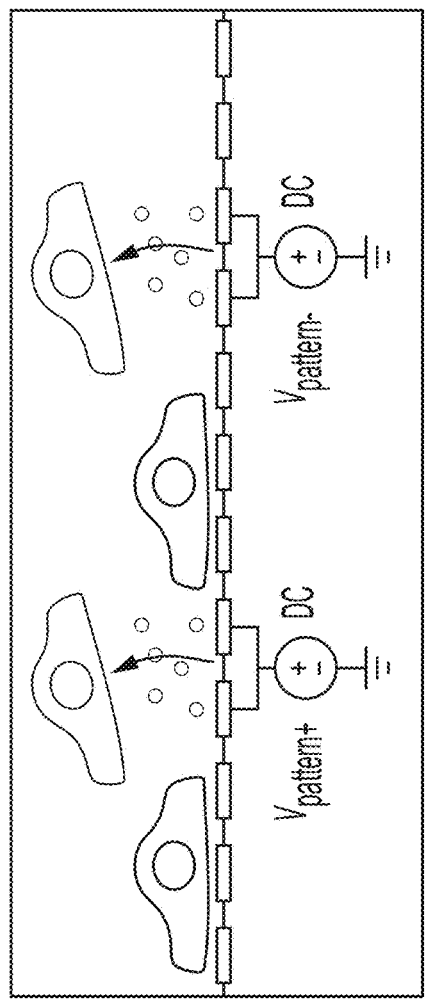
FIG. 13A-D is a series of diagrams illustrating variations of cell patterning using an electrode array.
Figure 13D:
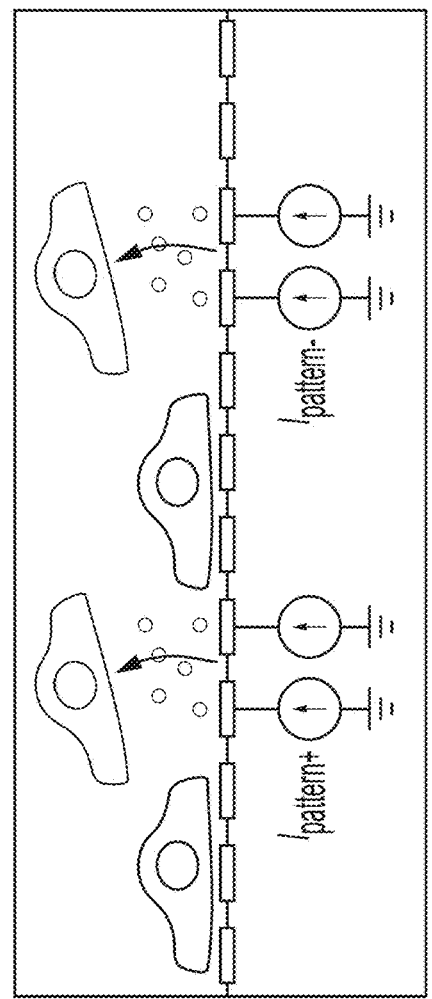
Figure 13A:
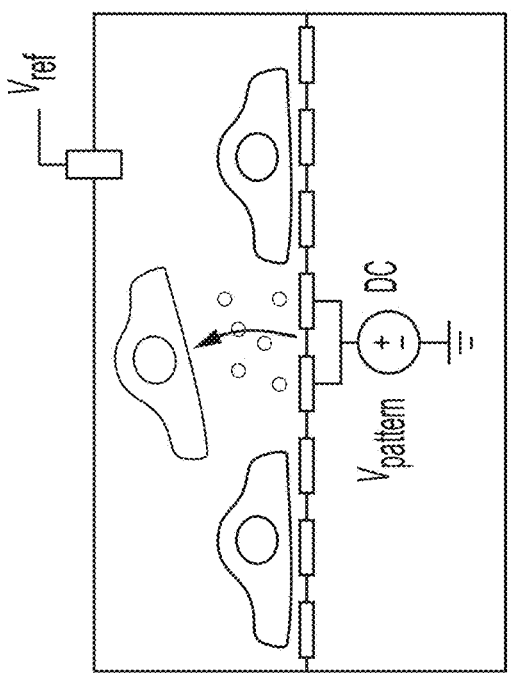
Figure 13C:
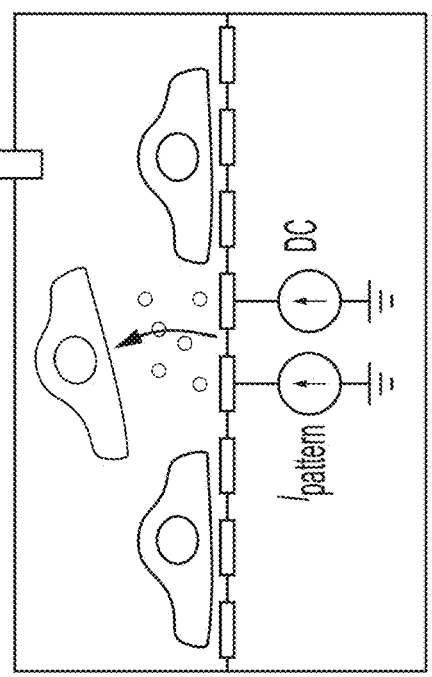

A CMOS electrode array as shown in FIG. 12, MDCK cells, and $H_2$ gas generation are used in this example. In this experiment, $H_2$ gas was generated by applying −1.25 V to the platinum electrodes versus a Ag/AgCl pseudo reference electrode. FIG. 12 shows fluorescent microscope images of before (middle) and after (right) patterning voltage is applied for 80 seconds, and show that the pattern in cells was defined successfully based on the pattern of electrodes. With the electrode pitch of 20 μm, square holes of various sizes were made in the uniform cell sheet with high spatial resolution, as confirmed using nuclei fluorescent markers and fluorescent imaging.

Figure 14:
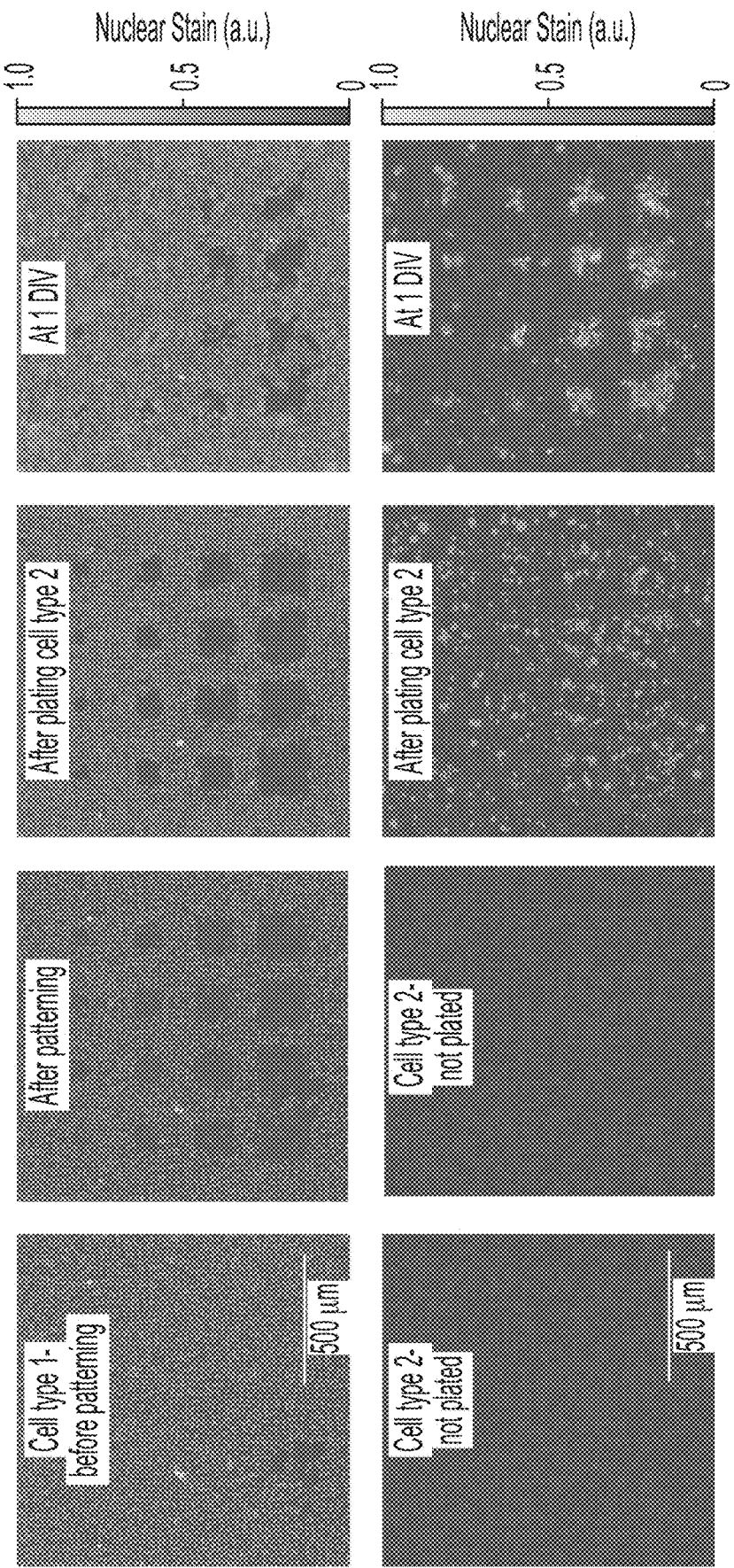
FIG. 14 shows a series of fluorescent microscope images illustrating the process of defining a co-culture via patterning and then plating a second cell type.

FIG. 14 shows a series of fluorescent microscope images illustrating the process of defining a co-culture via patterning and then plating a second cell type. The cell types were distinguished by different nuclei fluorescent markers. In the experiment in FIG. 14, a co-culture of two different cell types was defined by plating a second MDCK cell line with a different nuclei fluorescent marker after the initial patterning. The second cell type filled in the generated space, showing the ability to spatially define co-cultures with high spatial resolution. Further patterning and plating could also be performed to define multiple cell co-cultures and patterns in a bottom-up approach.

Example 9: Directed Cell Evolution by Removing Culture Heterogeneity

This example describes a method of directed cell evolution to eliminate cells from the cell culture whose properties are not desired.

Figure 15:
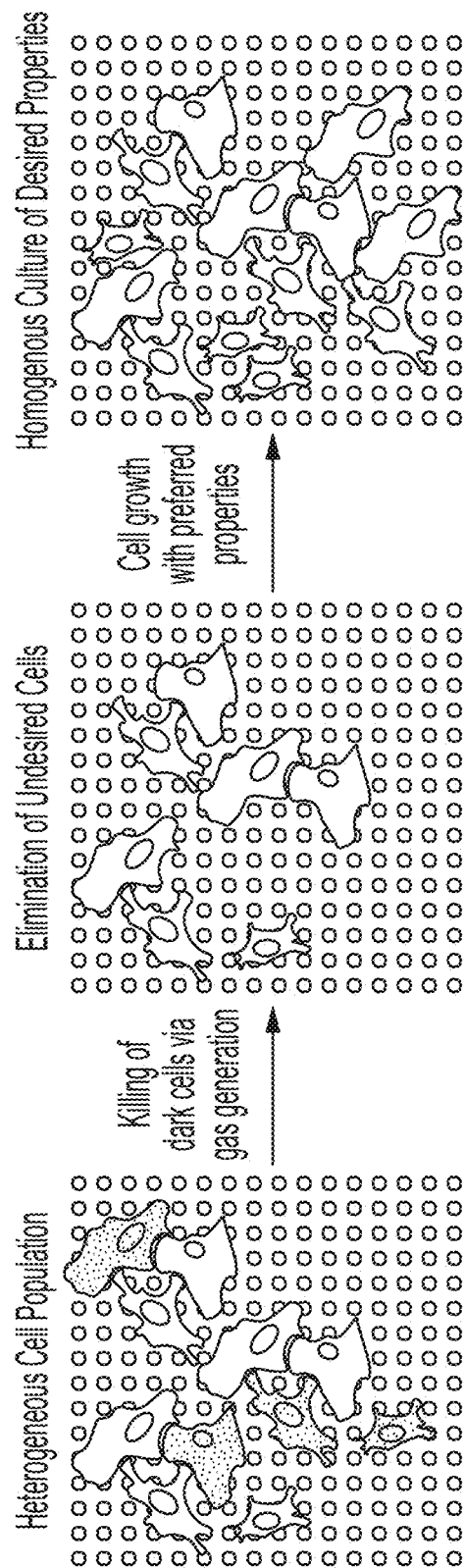
FIG. 15 is a series of schematic diagrams illustrating a heterogeneous cell population, elimination of undesired cells using patterned electrochemical gas generation on select electrodes, and a homogenous culture of desired properties after subsequent cell growth.

FIG. 15 is a series of schematic diagrams illustrating a heterogeneous cell population, elimination of undesired cells using patterned electrochemical gas generation on select electrodes, and a homogenous culture of desired properties after subsequent cell growth. The choice of which cells to eliminate can be made via optical imaging or via other properties measured using the electrode array. The capability to eliminate cells from the culture without having to remove from the culture plate is advantageous over current processes which would require suspending the cells and separating using a cell sorting machine with a further replating step to again culture, or removal of single cells with the desired properties using a micropipette and then replating. Furthermore, the lineage of the cell history can be preserved as the spatial location of each cell does not change as the cells remain adhered during the process. Such an elimination process could also be used for further analyses to be performed to on a subset of cells after culturing the electrode array, where cells unwanted for further measurement are first killed before cell suspension and removal.

Example 10: Wound Healing Assay

This example describes a combined application of both the cross-electrode impedance mapping and cell patterning is a wound healing assay.

These assays gauge cell growth rate and metabolism and can be useful for screening drugs affecting these parameters. Compared to the electrochemical patterning described herein, other tools mechanically generate a wound in a cell culture via a mechanical scratch which is both difficult to control and limiting in terms of wound pattern.

Figure 16:
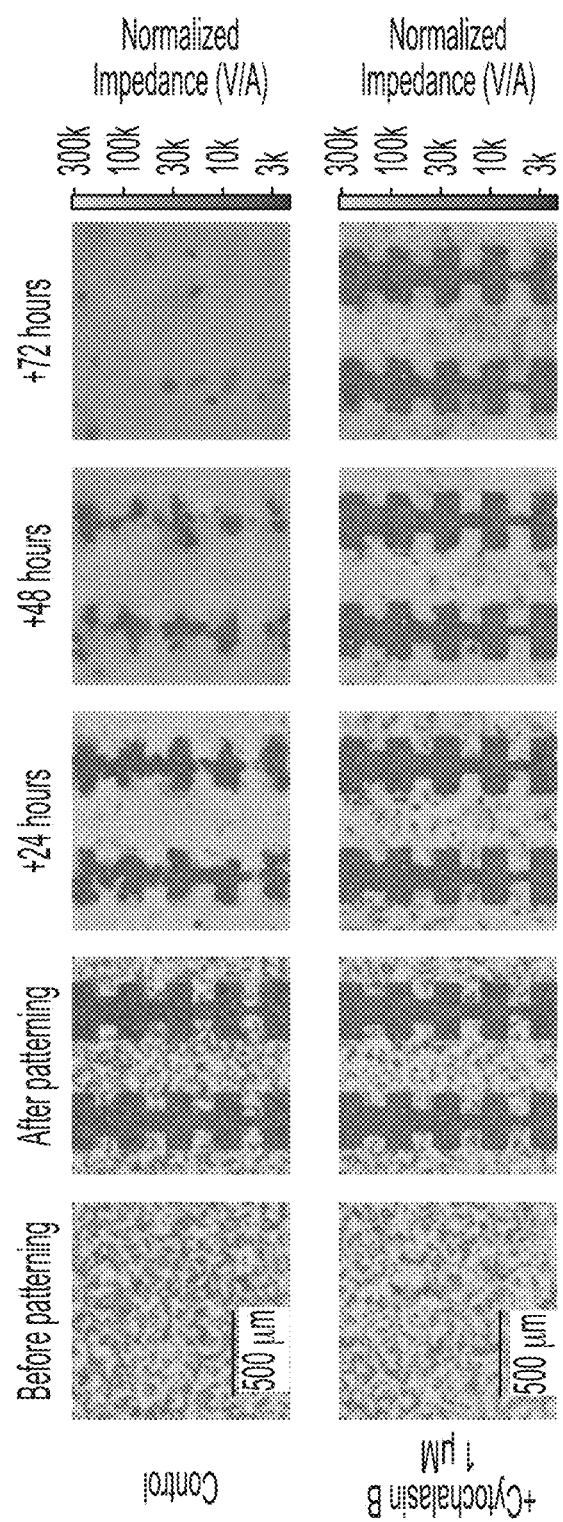
FIG. 16 illustrates an example of wound healing assay.
Figure 17C:
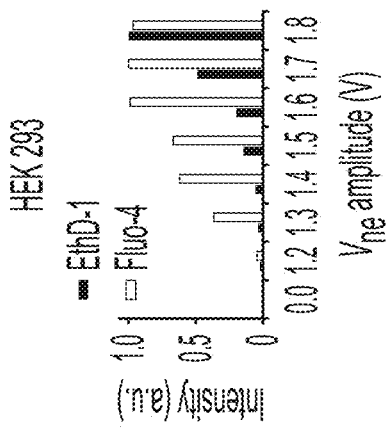
FIG. 17a-d illustrates an experiment demonstrating permeabilization techniques.
Figure 17D:
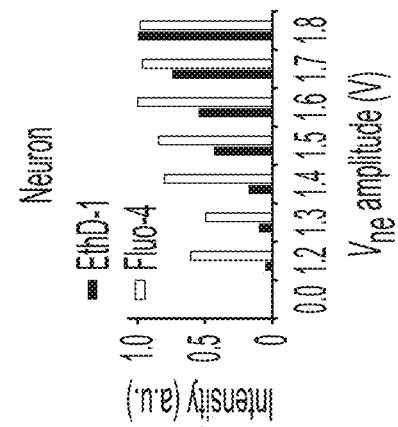
Figure 17A:
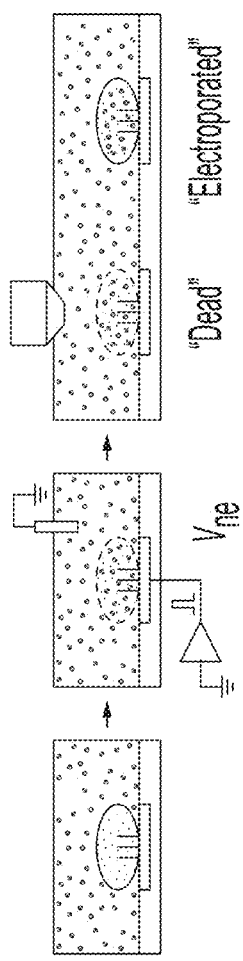
Figure 17B:
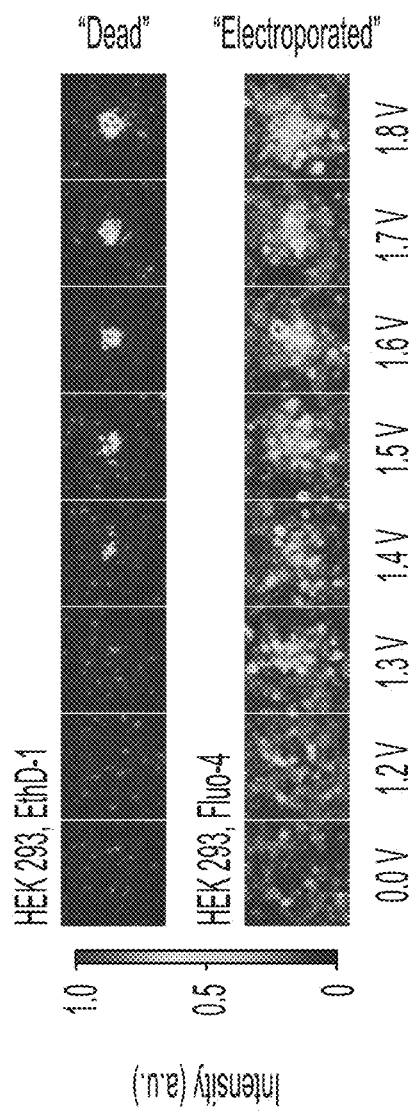

In this example, a wound is made in MDCK cells and then the growth is mapped in real-time. FIG. 16 shows a sawtooth-like pattern in the cells defined in the center of the device surface with varying distances of separation. These patterns were defined by applying electrode currents of −10 nA for 40 s versus a Ag/AgCl pseudo reference electrode. The regrowth of the culture was then measured using the impedance mapping method. A typical cell culture took ~3 days to fill in the wound whereas a culture with a growth inhibition drug showed very little regrowth. As illustrated by the normalized cross-electrode impedance maps in FIG. 16, the control culture shows regrowth after 72 hours in culture. A second culture with a drug that slows growth, cytochalasin B (1 µM), shows very little growth over the course of 72 hours, demonstrating the ability of the assay for drug screening.

Example 11: Molecular Delivery

This example describes a technique using planar electrodes for membrane permeabilization and molecular delivery. Unlike electroporation, which applies a concentrated electric field to break down the cell membrane, planar electrode permeabilization works via gas bubble formation, similar in concept to the patterning techniques discussed herein. Unlike patterning cells, where cells are killed to perform the patterning, for molecular delivery smaller holes are created on the cells that will then reseal over time.

FIG. 17 illustrates an experiment demonstrating permeabilization techniques using nanowire electrodes, while aspects of the technique may also be applicable using an electrode array using planar electrodes. In the experiment shown in FIG. 17, Fluo-4, a live assay, is dissolved in the extracellular solution (left panel, FIG. 17*a*). Electroporation protocols are applied to the nanoelectrodes using the pixel stimulator (middle panel, FIG. 17*a*) and allowed to recover in the Fluo-4. If successfully electroporated, Fluo-4 permeates into the cell. After recovery, a dead assay, EthD-1 is dissolved in the extracellular solution to reveal if cells have died due to irreversible electroporation (right panel, FIG. 17*a*). Cells that are successfully electroporated and recover retain Fluo-4 for imaging. FIG. 17*b* shows a heat maps showing the EthD-1 and Fluo-4 intensity averaged across eight investigated protocols of increasing voltage amplitude (3 trains of 5 biphasic pulses at 20 Hz) performed with HEK 293 cells. The CNEA array is divided into subgroups of 128 pixels for each of the eight protocols and repeated in a grid across the array. Imaging is performed on each pixel and the 128 images for each protocol are averaged together. FIG. 17*c* shows the averaged intensity results from FIG. 17*b* for the HEK 293 cells. Successful electroporation is viewed starting at ~1.3 V, whereas irreversible electroporation starts ~1.7 V. FIG. 17*d* shows results with neurons for the same test conditions show a lower threshold for successful electroporation, <1.2 V, and irreversible electroporation ~1.5 V.

Figure 18A:
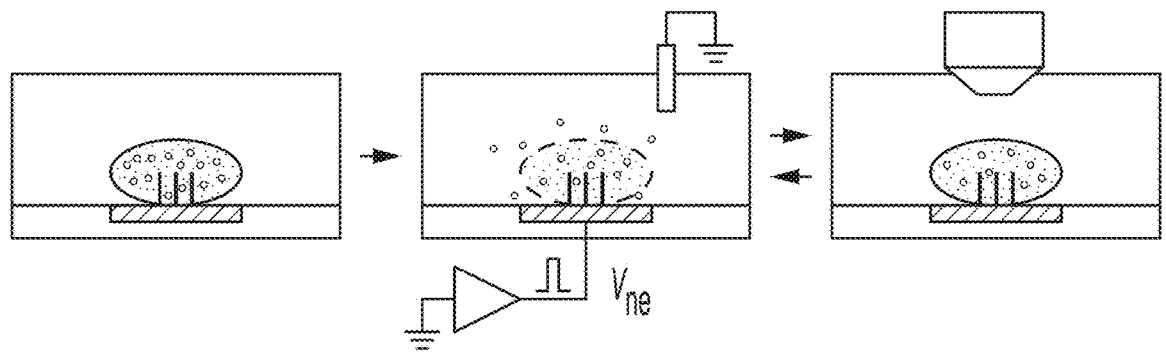
FIG. 18A-B illustrates an experiment using electroporation protocols, in which Fluo-4 is injected into the cell using Fluo-4 AM.
Figure 18B:
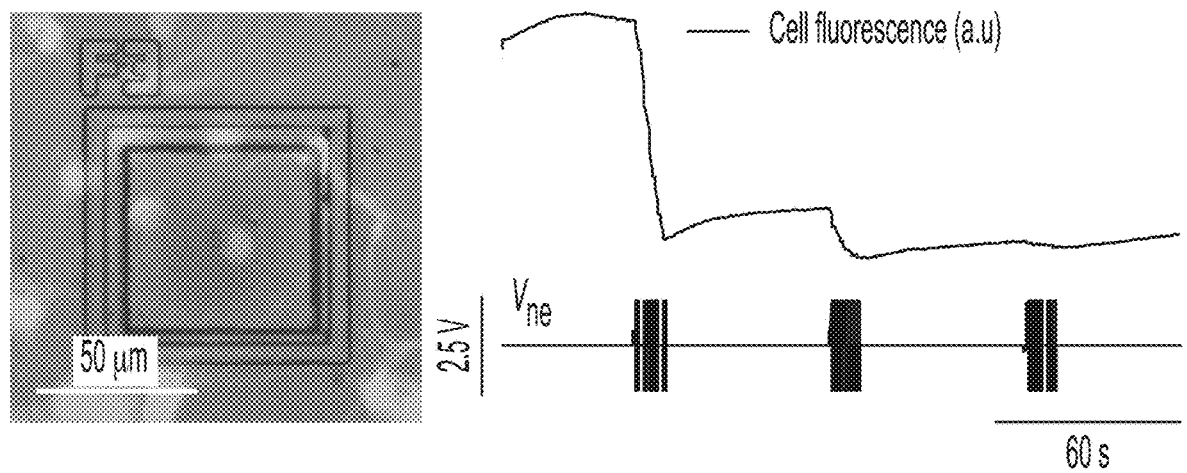

FIG. 18 illustrates another experiment, in which Fluo-4 is injected into the cell using Fluo-4 AM. Electroporation protocols are applied to the nanoelectrodes using the pixel stimulator (middle) while the fluorescence is monitored. If successfully electroporated, Fluo-4 is able to flow out of the cell causing a decrease in fluorescence. For successful protocols, the cell membrane recovers after electroporation (right panel, FIG. 18*a*). FIG. 18*b* illustrates an example of using a neuron with its fluorescence and applied electroporation signal. During electroporation, the fluorescence drops. Immediately afterwards, the cell membrane recovers and causes the fluorescence to plateau. The electroporation signals may be applied multiple times without affecting cell viability.

In both experiments shown in FIG. 17 and FIG. 18, it was observed that voltage signals needed to be of a certain duration, at least >50 ms, to see any permeabilization/delivery. This points to the need for Faradaic processes to generate gas bubbles, as the voltage needed is also comparable to the water window voltages ($H_2$ & $O_2$ gas generation via water splitting) with the platinum electrodes used. In FIG. 18, such a permeabilization signal is shown to be effective by causing transient leakage of a fluorescent dye, while in FIG. 17, a fluorescent dye is delivered to the cells.

Such delivery capabilities can be readily used for screening membrane impermeable compounds for their effects on cells and cell-to-cell interactions. The spatial capabilities of the electrode array, in which cells can be chosen for delivery, can be useful in this latter application of cell-to-cell interactions where the delivered cell and its undelivered neighbors can be measured for the effects of the compounds. Without such delivery capabilities, the membrane impermeable compounds would otherwise need to be chemically modified for delivery, which is expensive and time-consuming, or delivered using a micropipette on a single-cell basis, which is also expensive and time-consuming. Beyond compounds, RNA/DNA/plasmids can also be delivered for applications to synthetic biology.

Example 12: Serial Delivery for Cross-Effect Analysis

This example describes a multi-step delivery of compounds in cells using an electrode array.

Figure 19:
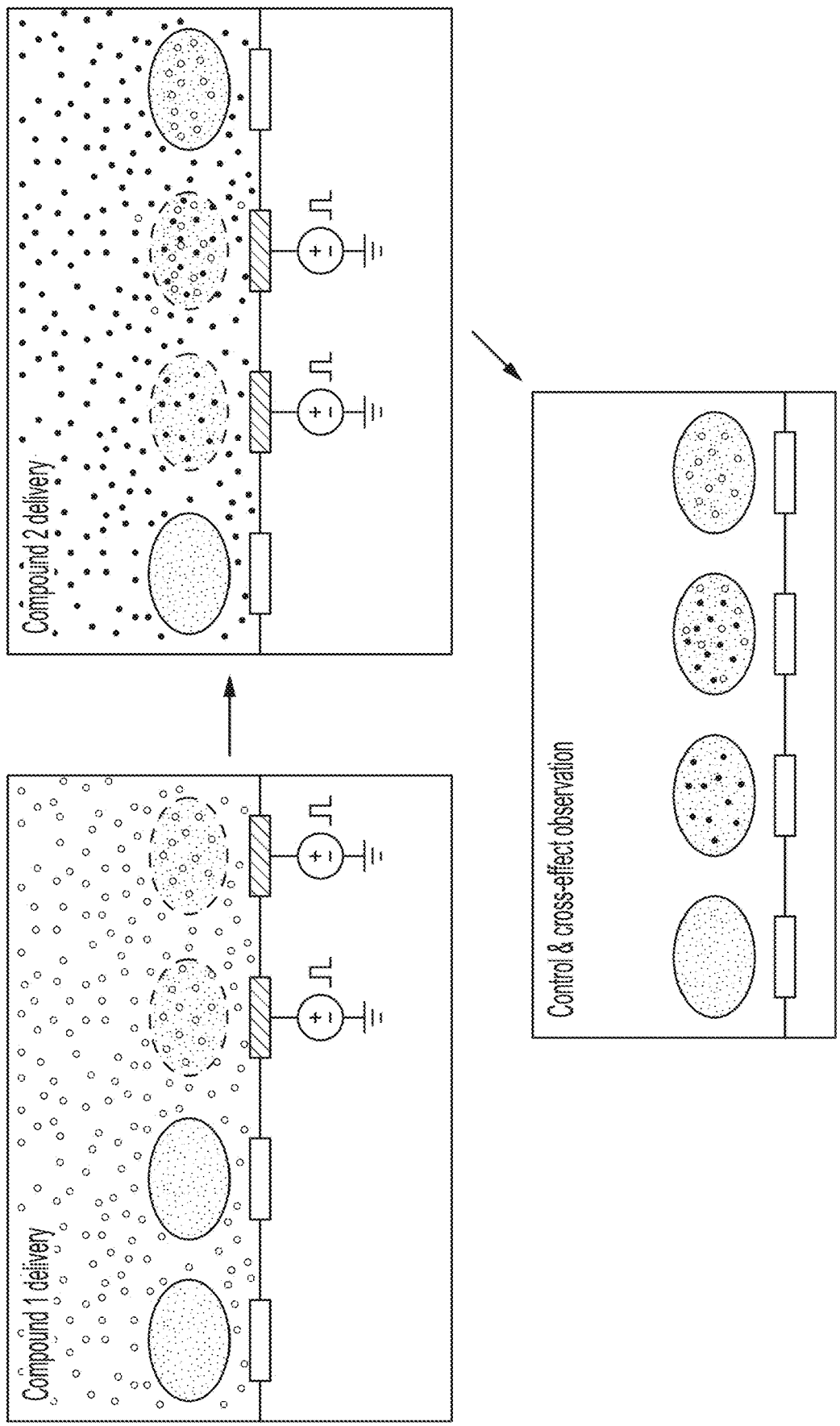
FIG. 19 shows a series of schematic diagrams illustrating generation of a control and cross-effect delivery using spatial addressing and serial delivery via gas generation.

FIG. 19 shows a series of schematic diagrams illustrating generation of a control and cross-effect delivery using spatial addressing and serial delivery via gas generation. As the electrode's properties are not modified during the gas evolution, in combination with the spatial capabilities of the addressable electrodes offers a further advantage of cross-compound effect screening. For example, if two compounds are desired to be investigated for their effects on cells, just two compound delivery steps are needed to form a complete matrix of drug effects.

Example 13: Extracellular Electrochemical Mapping

This example describes electrochemical mapping using redox electrochemistry on the electrode array.

Electrochemical measurements of cells using electrodes can use a single, large working electrode to measure bulk concentrations of analytes in solution. Such electrochemical electrode-based measurements include the Clark electrode for dissolved oxygen concentration measurement and hydrogen ion concentration (pH) measurement. According to an aspect of the present disclosure, an array of electrochemical electrodes may be used to spatially map analyte concentrations measured via electronics within a CMOS integrated circuit. Such electrochemical mapping can then be applied for cell analysis of cells cultured directly on top of the electrode array.

In this example, to demonstrate the capability for electrochemical mapping using an array of electrodes measured using a CMOS integrated circuit, cyclic voltammetry is performed using a common redox couple of ferricyanide/ferrocyanide, $[Fe(CN)_6]^{3-}/[Fe(CN)_6]^{4-}$.

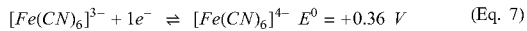

$$[Fe(CN)_6]^{3-} + 1e^- \rightleftharpoons [Fe(CN)_6]^{4-} \quad E^0 = +0.36\ V \quad \text{(Eq. 7)}$$

Figures 20A, 20B:
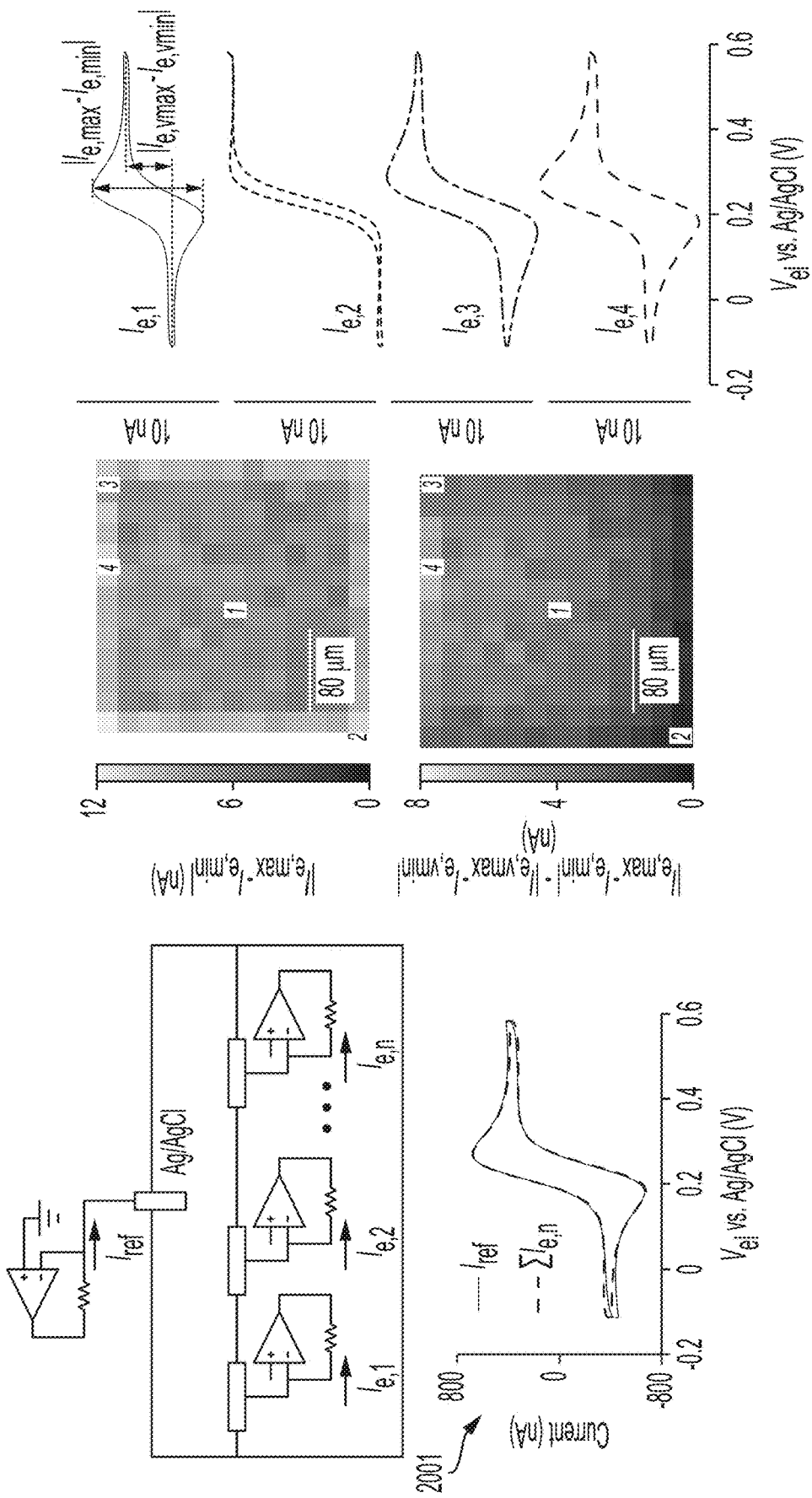
FIG. 20a-b illustrates an example of extracellular electrochemical mapping.

FIG. 20a is a schematic diagram showing the cyclic voltammetry configuration using CMOS integrated transimpedance amplifiers to measure each Pt electrode's current and an external transimpedance amplifier to measure the current through a Ag/AgCl pseudo reference electrode. In the experiment in FIG. 20a, a cyclic voltage ramp was applied at a scan rate of 35 mV/s with 1.5 M KCl+5 mM K3[Fe(CN)6]. The sum of the 13×13 electrodes' currents is used for the measurement, which equals that of the reference electrode. FIG. 20b show two spatial maps of the max range of the electrodes' currents ($|I_{e,max}-I_{e,min}|$; top left) which is related to the diffusion of ferricyanide (starting reactant), and the max range of currents minus the max/min voltage currents ($||I_{e,max}-I_{e,min}|-|I_{e,vmax}-I_{e,vmin}|$; bottom left) which is related to the ferrocyanide diffusion (product). Example individual electrode recordings are shown in FIG. 20b on the right with these parameters defined. The non-radial ferrocyanide diffusion is attributed to convection effects in solution.

In this experiment, a subset 13×13=169 of a 64×64 array of electrodes was connected to the same number of respective transimpedance amplifiers with a cyclic linear voltage ramp applied, as illustrated in the schematic diagram in FIG. 20a. FIG. 20b show spatial maps of the current density that show increased cathodic and anodic current magnitudes on the edges of the electrode, which may be attributed to increased radial diffusion/mass transport of the edge in comparison to the planar diffusion of center electrodes. Likewise, generation of products limits current density which is visualized by the peak current range minus the voltage maximum/minimum current range, as illustrated in the data plot 2001 in FIG. 20. The cyclic voltammetry data plot 2001 shows a tendency for product diffusion towards the upper right corner. The spatial measurement of such current shows the capability for current-based electrochemical mapping.

The open-circuit potential of the electrodes can also be used to measure the concentration of chemical species in solution. For a high-concentration of a redox couple in solution, the open-circuit potential of platinum electrodes in solution can be determined by the Nernst equation. The Nernst equation relates the reduction potential of an electrochemical reaction to the standard electrode potential, temperature, and activities of the chemical species undergoing reduction and oxidation,

$$Ox + ne^- \rightleftharpoons Red \quad \text{(Eq. 8)}$$

$$E_H = E^0 - \frac{\varphi_t}{n} \ln \frac{[Red]}{[Ox]}$$

where $E_H$ is the electrode voltage potential with respect to the standard hydrogen electrode (S.H.E), $E^0$ is the half-cell reduction potential, q, is the thermal voltage (~25.7 mV at 25° C.), [Ox]/[Red] is the concentration of the oxidized/reduced chemical species, and n is the number of electrons transferred in the cell half reaction. For the ferricyanide/ferrocyanide reaction, measurement of the open-circuit potential then reflects the ratio of the concentrations of these ions in solution.

In this example, the potential of the remainder of the electrode array was measured. In particular, ferrocyanide generation and transport across a CMOS electrode are mapped using open circuit potential.

A cyclic potential is applied to a group of 13×13 electrodes (with 9 electrodes excluded within the group of 13×13 electrodes, as illustrated in FIG. 21b) while the remaining electrodes' open circuit potentials are measured. FIG. 21a are data plots that show select electrode voltages, $V_{el}$, plotted over time, which shows an increase and decrease related to the ferricyanide/ferrocyanide concentrations. FIG. 21b is a heat map that illustrates for one cycle, the overall amplitude (maximum minus the minimum) of the open circuit potential plotted across the array to show diffusion/mass transport which tends towards the upper left corner. FIG. 21c shows a heat map and a data plot that illustrate the minimum time of the open-circuit potential plotted versus distance from the center of the 13×13 electrodes showing the transient aspects of the diffusion/mass transport.

In summary, for the cyclic voltammetry, measuring the open-circuit around the electrode shows the flow of ferrocyanide towards the upper right corner of the device.

Example 14: Electrochemical Oxygen Mapping of Cells

This example describes a technique applying electrochemical mapping to cell analysis. For example, a Clark electrode based on platinum may be measured by applying a pulsed voltage or a voltage pulse sequence which sequentially oxidizes and then reduces the platinum. As platinum oxide blocks oxygen reduction, the current drops to zero after the oxide is formed. When the oxide is then reduced, the platinum electrode passes a negative current due to the presence of oxygen,

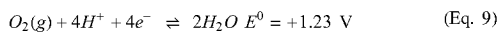

$$O_2(g) + 4H^+ + 4e^- \rightleftharpoons 2H_2O \; E^0 = +1.23 \text{ V} \qquad \text{(Eq. 9)}$$

The local oxygen concentration is then consumed, and the electrode waits for the further diffusion of additional oxygen to the electrode to pass current. Therefore, the rate of the equation is limited by oxygen diffusion which is proportional to the oxygen concentration in solution and can be measured by measuring the electrode current.

Figure 22B:
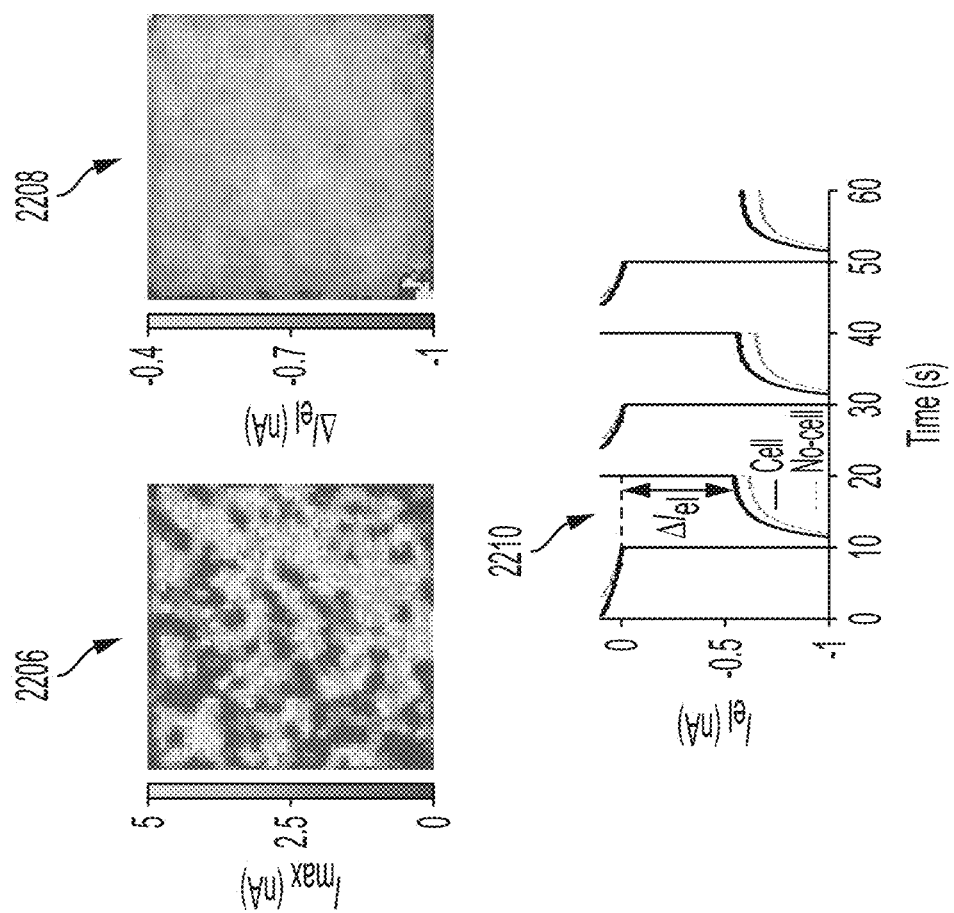
FIG. 22a-b illustrates an example of electrochemical oxygen mapping of cells.
Figure 22A:
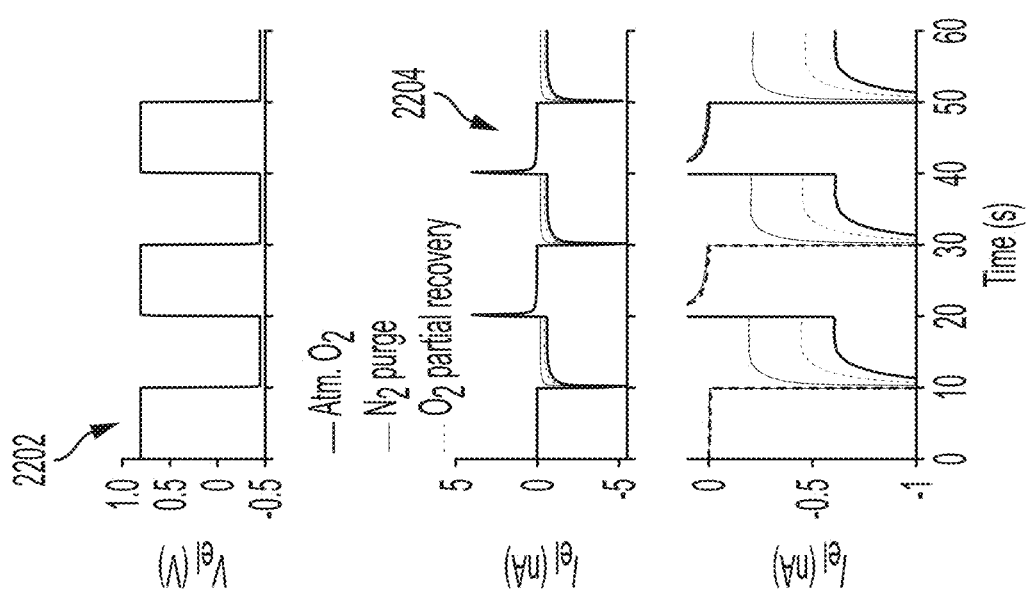

In an experiment using an electrode array, a measurement was performed using a salt solution (phosphate-buffered saline) exposed to ambient air and then subsequently purged with nitrogen gas to reduce the oxygen concentration. FIG. 22a shows a voltage pulse sequence 2202 applied to stimulation electrodes in the electrode array, and a series of data plots 2204 of measurement using the CMOS electrode array in ambient air, with a partial nitrogen purge, and a partial recovery ($N_2$ purge stopped), respectively. The data plots 2204 show that the electrode current reflects the oxygen concentration.

Comparing the current $I_{el}$ before and after the purging shows a marked reduction. Experiments were then performed with HEK293 cells, and the results are shown in FIG. 22b. FIG. 22b shows a cross-electrode impedance heat map 2206 using cross-electrode max current $I_{max}$ over the electrode array area, and a heat map 2208 of a change in electrode current $\Delta I_{el}$ over the electrode array area. The same style of oxygen measurement with HEK293 cells shows a decrease in oxygen concentration where the cells are located, as confirmed with an impedance map.

Cells consume oxygen as a part of aerobic metabolism, therefore the oxygen concentration around cells is smaller than places without cells. Indeed, mapping the electrode current across the array shows the location of the cells has a smaller magnitude of current than places without cells, as imaged using a cross-electrode impedance map. The left and bottom edges of map 2208 also show a larger magnitude of current, which is attributed to edge effects and the increased diffusion/mass transport.

Figures 26E, 26F:
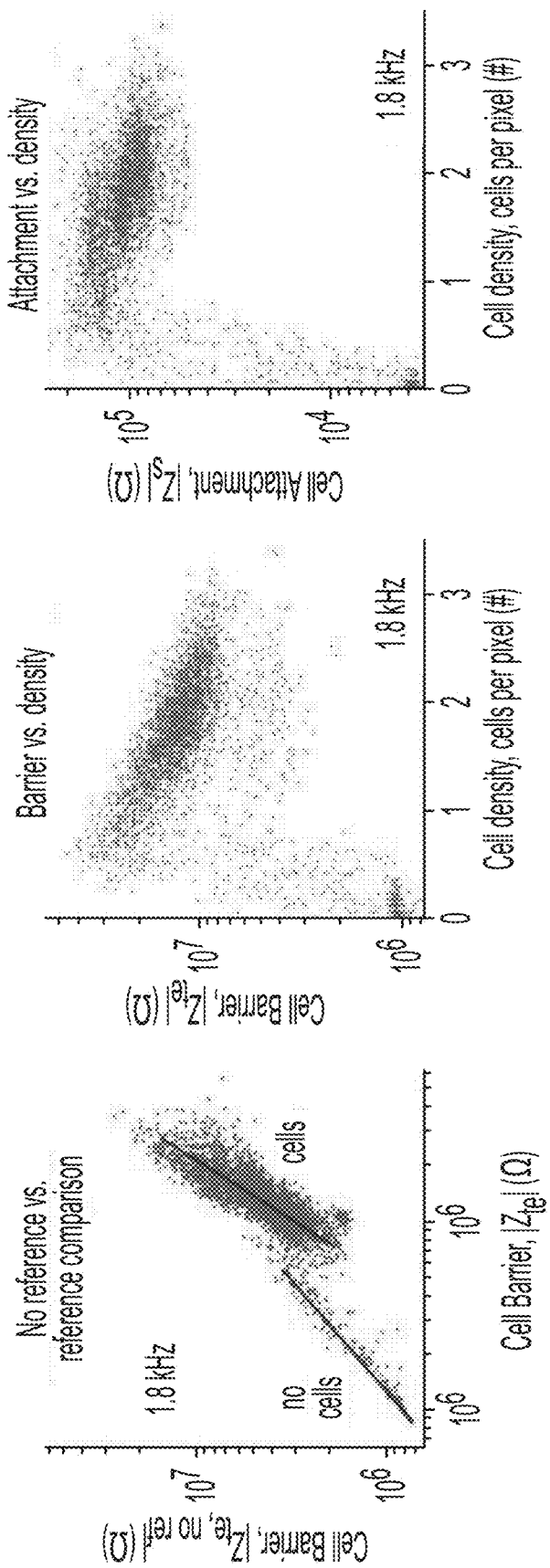
FIG. 26e shows a comparison between $Z_{te}$ measured without and with a reference.
FIG. 26f shows a comparison between $Z_{te}$ and $Z_s$ versus extracted cell density.

Example 15: Effects of Platinum Black and Frequency on Cell Barrier Sensitivity In this example, platinum black (PtB) was used to lower the electrode impedance, $Z_e$, to improve cell barrier measurement sensitivity. FIG. 26a shows results of a comparison study of electrode impedance for cells cultured at ~72 hours with electrodes under three scenarios: low-density, high-density, and without cells. FIG. 26b is a data plot illustrating that PtB lowered the $Z_{te}$ measurement of bare electrodes by about 5×, allowing the cell-cell connections of the two different densities to be measured with higher signal-to-noise. FIG. 26c illustrates cell barrier maps versus a reference at different frequencies. The lower frequency measurements show more spread and do not capture the cell sheet edge but the 1.8 kHz measurement showed the highest contrast for the cell-connection measurement when compared to density maps extracted from imaging. FIG. 26d shows cell density and connectivity maps extracted from the nuclei of the fluorescence images. FIG. 26e shows a comparison between $Z_{te}$ measured without and with a reference at 1.8 kHz. Slightly smaller $Z_{te}$ is measured without the reference, but for regions with cells and without (the two clusters) the relationship is direct. Measurements without the reference are preferred, as the $Z_e$ contribution can be easily subtracted from the cell-substrate attachment measurement. FIG. 26f shows a comparison between $Z_{te}$ and $Z_s$ versus extracted cell density. For this comparison, $Z_s$ is down-sampled via a bilinear interpolation to have the same spatial resolution as the $Z_{te}$ measurement. The cell barrier shows a stronger dependence on cell density due to its measurement geared towards cell-cell connectivity. There's a small correlation between $Z_s$ and cell density as well, which can be seen from the cell-circuit model (FIG. 4B) as having an effect if $Z_s$ is high and the assumption that $Z_s << Z_{te}$ no long holds which was used in the $Z_s$ calculation.

Having thus described several aspects of at least one embodiment of this invention and examples thereof, it is to be appreciated that various alterations, modifications, and improvements will readily occur to those skilled in the art. Such alterations, modifications, and improvements are intended to be part of this disclosure, and are intended to be within the spirit and scope of the invention. Further, though advantages of the present invention are indicated, it should be appreciated that not every embodiment of the technology described herein will include every described advantage. Some embodiments may not implement any features described as advantageous herein and in some instances one or more of the described features may be implemented to achieve further embodiments. Accordingly, the foregoing description and drawings are by way of example only.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The terms "approximately" and "about" may be used to mean within ±20% of a target value in some embodiments, within ±10% of a target value in some embodiments, within ±5% of a target value in some embodiments, and yet within

What is claimed is:

1. A method for providing spatially positioned electrochemical reactions with an electrode array exposed on a surface of a semiconductor substrate, the method comprising:
   selecting one or more electrodes in the electrode array;
   controlling circuitry in the semiconductor substrate to apply, at the one or more electrodes, one or more stimulus signals to initiate an electrochemical reaction at the selected one or more electrodes; and
   measuring, with the circuitry, a value of an electrical characteristic at each of some or all remaining electrodes in the electrode array that are outside the selected one or more electrodes.

2. The method of claim 1, wherein the electrochemical reaction is a half reaction that generates a gas in a solution, and wherein the one or more stimulus signals comprise potentials that are above a redox potential for generation of the gas.

3. The method of claim 2, wherein the solution comprises a plurality of cells attached to the surface of the semiconductor substrate, and the method further comprises:
   generating the gas at the selected one or more electrodes such that at least one cell of the plurality of cells that is disposed on the selected one or more electrodes is detached from the surface of the semiconductor substrate.

4. The method of claim 3, further comprising:
   mapping a time sequence of regrowth of the plurality of cells on the surface at positions where the at least one cell has detached from; and
   based on the mapping, determining a growth rate of the plurality of cells.

5. The method of claim 1, wherein controlling circuitry to apply one or more stimulus signals comprises performing cyclic voltammetry at the selected one or more electrodes, and the method further comprises:
   generating a map of electrical characteristics based on the result of the measuring.

6. The method of claim 5, wherein the electrical characteristic is a characteristic of an open-circuit potential.

7. The method of claim 5, wherein the electrical characteristic is a current.

8. The method of claim 7, wherein the characteristic of the current is a maximum extent of a range of a cyclic current.

9. The method of claim 1, wherein controlling circuitry to apply one or more stimulus signals comprises applying a pulsed voltage signal at an electrode of the selected one or more electrodes, wherein
   during a first portion within the pulsed voltage signal, the electrode is being oxidized, and during a second portion of the pulsed voltage signal, an oxide on the electrode is being reduced, and the method further comprises:
   measuring, with the circuitry, a current signal at the electrode during the second portion of the pulsed voltage signal;
   based on a time rate of change of the current signal, determining an oxygen concentration at a position of the electrode; and
   generating a map of oxygen concentration based on the result of the determining.

10. The method of claim 1, wherein the one or more stimulus signals are potentials that are relative to a potential of a reference electrode.

11. A system comprising:
   a semiconductor substrate comprising:
      an electrode array including a plurality of individually addressable electrodes disposed on a surface of the semiconductor substrate; and
      circuitry that is controllable by one or more processors to apply, at a group of electrodes in the electrode array, one or more potentials relative to a potential of an electrode in the electrode array or a potential of a reference electrode to initiate an electrochemical reaction at the group of electrodes, wherein
      the circuitry comprises a plurality of recording circuits, each recording circuit configured to measure a current at an electrode of the electrode array.

12. The system of claim 11, wherein the electrode array comprises a plurality of pads disposed on an insulative surface of the semiconductor substrate.

13. The system of claim 11, wherein the plurality of individually addressable electrodes comprises Au or Pt.

14. The system of claim 11, wherein the reference electrode is a Ag/AgCl reference electrode.

15. The system of claim 11, wherein the electrode array comprises at least 1000, at least 4000, or at least 1,000,000 electrodes.

16. The system of claim 15, wherein the plurality of recording circuits comprises at least 10 recording circuits, or at least 4000 recording circuits.

17. The system of claim 15, wherein each recording circuit comprises a transimpedance amplifier (TIA).

18. The system of claim 17, wherein the TIA comprises an impedance component having a resistance of at least 10 MΩ, wherein an output voltage of the TIA is proportional to a voltage across the impedance component.

19. The system of claim 18, wherein the impedance component comprises a switching capacitor.

20. A system for providing spatially positioned electrochemical reactions, the system comprising:
   an electrode array exposed at a surface area of a semiconductor substrate;
   circuitry disposed in the semiconductor substrate and coupled to the electrode array;
   at least one non-transitory computer-readable medium having stored thereon executable instructions; and
   at least one processor programmed by the executable instructions to perform a method comprising acts of:
   selecting a pattern of electrodes in the electrode array; and
   controlling circuitry to:
      apply, at the pattern of electrodes, one or more stimulus signals relative to a potential or current of an electrode in the electrode array or a potential or current of a reference electrode, such that an electrochemical reaction is initiated at the pattern of electrodes, and to
      measure a value of an electrical characteristic at each of some or all remaining electrodes in the electrode array that are outside the pattern of electrodes.

* * * * *